(12) United States Patent
Schrader et al.

(10) Patent No.: US 11,981,035 B2
(45) Date of Patent: May 14, 2024

(54) MEDICAL HANDLING DEVICE AND METHOD FOR CONTROLLING A HANDLING DEVICE

(71) Applicant: KARL STORZ SE & Co. KG, Tuttlingen (DE)

(72) Inventors: Stephan Schrader, Tuttlingen (DE); Benedikt Koehler, Tuttlingen (DE); Chang-Hae Kim, Tuttlingen (DE); Marco Schulze, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 276 days.

(21) Appl. No.: 16/903,690

(22) Filed: Jun. 17, 2020

(65) Prior Publication Data
US 2020/0397225 A1 Dec. 24, 2020

(30) Foreign Application Priority Data
Jun. 19, 2019 (EP) .................................. 19 181 322

(51) Int. Cl.
*A61B 1/00* (2006.01)
*A61B 1/045* (2006.01)
(Continued)

(52) U.S. Cl.
CPC ......... *B25J 9/1689* (2013.01); *A61B 1/00006* (2013.01); *A61B 1/00045* (2013.01);
(Continued)

(58) Field of Classification Search
CPC ............ A61B 1/00039; A61B 1/00006; A61B 1/00009; A61B 1/00045; A61B 1/00149;
(Continued)

(56) References Cited

U.S. PATENT DOCUMENTS 5,696,837 A 12/1997 Green
9,516,996 B2 * 12/2016 Diolaiti .................. A61B 34/20
(Continued)

FOREIGN PATENT DOCUMENTS

DE 102015009507 A1 1/2017
DE 102015121017 A1 6/2017
(Continued)

OTHER PUBLICATIONS

Serefoglou, Stefanos et al. "Combined Endo- and Exoscopic Semi-Robotic Manipulator System for Image Guided Operations" Springer-Verlag Berlin Heidelberg; Available at https://link.springer.com/content/pdf/10.1007/11866565_63.pdf; 2006.
(Continued)

*Primary Examiner* — Timothy J Neal
*Assistant Examiner* — William B Chou
(74) *Attorney, Agent, or Firm* — Jason H. Vick; Sheridan Ross, PC

(57) ABSTRACT

A medical handling device comprises an instrument holder for holding an observation instrument that is equipped with an image capturing unit for capturing an image section. The handling device further comprises a robotic handling unit that supports the instrument holder and a control device that comprises a handling control unit for controlling the robotic handling unit and an instrument control unit for controlling the observation instrument. An input device is coupled to the control device for selecting an image section to be reproduced. The control device is adapted to control the robotic handling unit in response to user inputs at the input device to change the captured image section. The control device is adapted to convert operating commands at the input device into movement instructions, depending on a present orientation of the image capturing unit.

20 Claims, 12 Drawing Sheets

(51) Int. Cl.
    *A61B 1/05*     (2006.01)
    *A61B 34/35*     (2016.01)
    *A61B 34/37*     (2016.01)
    *B25J 9/10*     (2006.01)
    *B25J 9/16*     (2006.01)

(52) U.S. Cl.
    CPC ...... *A61B 1/00149* (2013.01); *A61B 1/00188* (2013.01); *A61B 1/00193* (2013.01); *A61B 1/045* (2013.01); *A61B 1/05* (2013.01); *A61B 34/35* (2016.02); *A61B 34/37* (2016.02); *B25J 9/106* (2013.01); *A61B 1/00009* (2013.01)

(58) Field of Classification Search
    CPC . A61B 1/00188; A61B 1/00193; A61B 1/045; A61B 1/05; A61B 34/35; A61B 34/37; B25J 9/106; B25J 9/1689
    See application file for complete search history.

(56) References Cited

U.S. PATENT DOCUMENTS

| | | | |
|---|---|---|---|
| 10,555,662 | B2 | 2/2020 | Hofer et al. |
| 10,645,372 | B2 | 5/2020 | Köhler et al. |
| 2003/0212308 | A1* | 11/2003 | Bendall ............... A61B 1/00052 600/102 |
| 2009/0248036 | A1* | 10/2009 | Hoffman ............ A61B 1/00149 606/130 |
| 2010/0274087 | A1* | 10/2010 | Diolaiti ................ A61B 34/30 700/275 |
| 2015/0085084 | A1 | 3/2015 | Heni et al. |
| 2017/0080574 | A1* | 3/2017 | Kuroda ................. A61B 34/35 |
| 2017/0163972 | A1 | 6/2017 | Köhler et al. |
| 2018/0263710 | A1 | 9/2018 | Sakaguchi et al. |
| 2019/0357751 | A1* | 11/2019 | Friedlander ............ A61B 1/015 |
| 2021/0145526 | A1* | 5/2021 | Robinson ............. A61B 34/35 |

FOREIGN PATENT DOCUMENTS

| | | |
|---|---|---|
| DE | 102016225689 A1 | 6/2018 |
| EP | 3135445 A1 | 3/2017 |

OTHER PUBLICATIONS

Extended European Search Report for European Application No. 19181322.9, mailed Jan. 7, 2020.

* cited by examiner

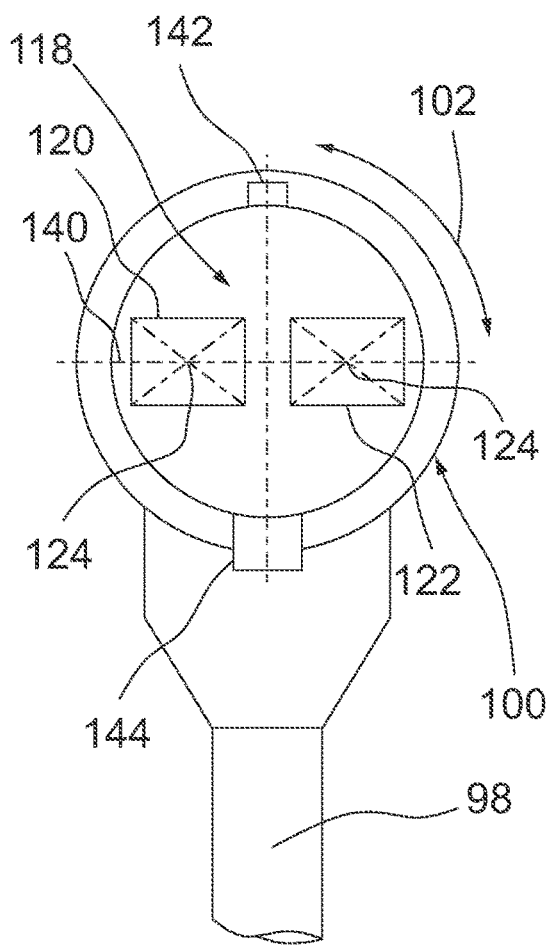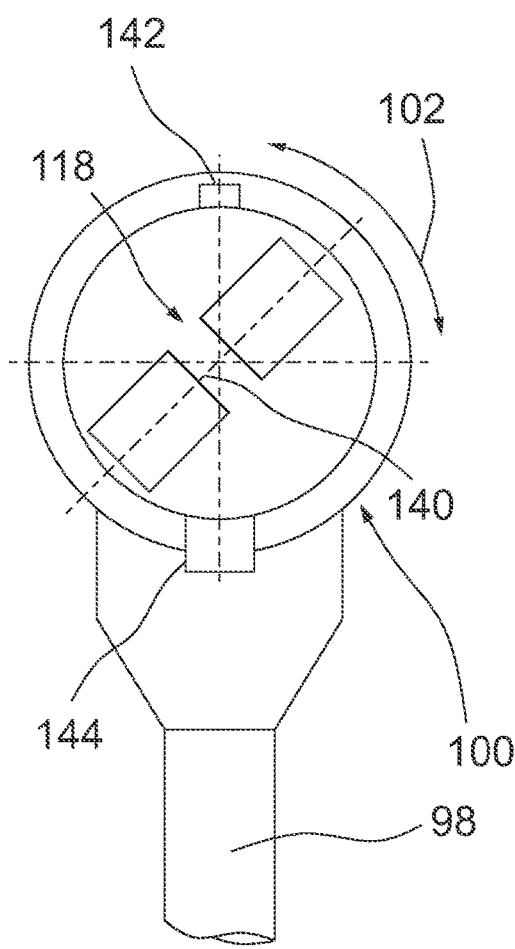
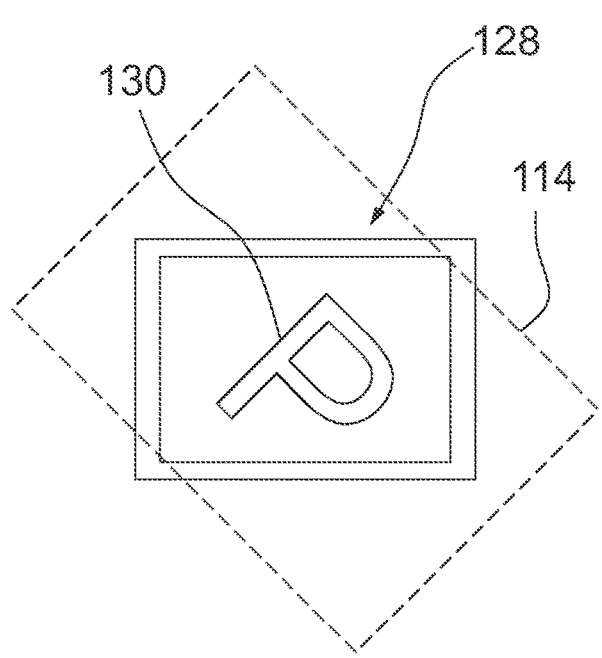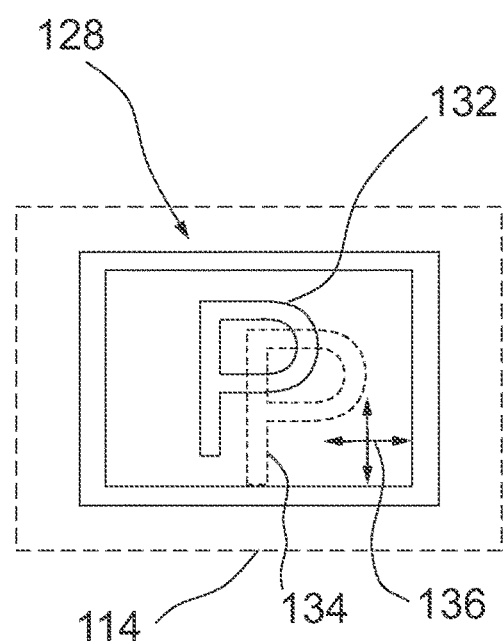
Fig. 3  Fig. 4

MEDICAL HANDLING DEVICE AND METHOD FOR CONTROLLING A HANDLING DEVICE

CROSS-REFERENCE TO RELATED APPLICATIONS

This application claims priority from European patent application 19 181 322.9, filed on Jun. 19, 2019. The entire content of that priority application is incorporated herein by reference.

BACKGROUND

The present disclosure relates to a medical handling device and a method for controlling a handling device, wherein the handling device comprises a robotic handling unit, which carries an instrument holder for holding an instrument, for example an observation instrument, and wherein a handling control device is provided for controlling the robotic handling unit, which can be controlled via an input device.

US 2015/0085084 A1 discloses a medical instrument that is designed arranged as an observation instrument, which is arranged to capture an image of an object field on a human or animal body from outside the body, the instrument comprising a shaft and observation optics arranged at a distal end of the shaft for capturing the image of the object field, wherein the observation optic is arranged as a stereo optic with at least one electronic image capturing unit for capturing a stereo image of the object field, and wherein the instrument comprises an optical unit, which comprises the observation optic, and which is rotatable about a first axis of rotation approximately parallel to a viewing direction of the observation optic.

Such an observation instrument for observing an object field from outside the body is referred to as an exoscope. Furthermore, instruments, for instance observation instruments, are known, which are arranged as endoscopes for capturing an image inside the human or animal body.

US 2017/0163972 A1 discloses an observation device, which comprises an observation instrument and an input device that is arranged as a multi-axis input module for controlling the observation instrument. The input device is designed similar to a so-called space mouse. US 2017/0163972 A1 discloses the use of the input device for controlling imaging parameters as well as for controlling image reproduction parameters. An imaging parameter involves for example a focus adjustment. An image reproduction parameter involves for example a digital zoom.

For the purposes of present disclosure, a distal end of an element is an end that faces an observation object, such as a patient. In contrast, a proximal end of the element is an element that is facing away from the distal end and thus also from the observation object. In the case of a hand-guided instrument, the proximal end regularly faces the operator of the instrument. In the case of an instrument that is guided by means of a handling unit, the instrument is occasionally—but not necessarily—accommodated in the region of its proximal end at the handling unit, for example at a housing.

Furthermore, so-called tele-operational systems or tele-manipulation systems are known, in which an instrument in the form of an observation instrument or the like is held and remotely controlled by a manipulator, for example from U.S. Pat. No. 5,696,837 A.

Medical instruments, such as observation instruments in the form of an endoscope or an exoscope, are often hand-held and/or hand-guided. This has the advantage that the user can intuitively and immediately adjust the direction of view, the object field and/or image section and other parameters of the image acquisition by positioning the instrument accordingly in space.

However, systems are also known, in which instruments are not hand-held or hand-guided, but are mounted on a tripod or boom. This has the advantage that no operator is required to hold the instrument manually in the desired position and orientation. It is conceivable that the instrument is arranged in a fixed position, for example, in order to permanently observe a certain same image section in a pre-selected object field during an operation.

Furthermore, it is also conceivable to arrange the instrument on a handling unit and/or manipulator (also referred to as a motorized holding system and/or robot) in order to use degrees of freedom of movement of the handling unit to move and align the instrument.

In this way, even if the instrument is not directly hand-held or hand-guided, the position, orientation and/or image section can be changed. However, this requires an operation to initiate the desired movement of the instrument.

Often, however, control elements are already provided for the instruments as such, e.g. control elements for controlling imaging parameters and/or image reproduction parameters of an image capturing system, which comprises an observation instrument having an image capturing unit, and a corresponding display for image reproduction. This means that even without additional movement of the instrument, various control operations are already conceivable, for which control elements are provided.

When automating and/or mechanically supporting medical activities, however, care must be taken to ensure that the systems as such are still intuitive, simple and safe to operate. For instance with telemedical systems and/or robotic systems, it must be considered that frequently no direct feedback to the operator is possible. This can lead to operating errors, in comparison to purely manual, hand-guided operation, if the operator is not immediately aware of the activity triggered by the operating command currently issued.

In view of this, it is an object of the present disclosure to present a medical handling device and a method for controlling a handling device, which enable intuitive and low-error control of a number of functions, at least in certain embodiments.

It is a further object of the present disclosure to present a medical handling device and a method for controlling a handling device that enable the use of a manageable number of input devices and/or input options to control a plurality of different functions, at least in certain embodiments.

It is a further object of the present disclosure to present a medical handling device and a method for controlling a handling device that prevent adverse interactions/interferences during operation, for instance in terms of operator control, at least in certain embodiments.

It is a further object of the present disclosure to present a medical handling device and a method for controlling a handling device that enable clear and concise operation and thus reduce the likelihood of operating errors, at least in certain embodiments.

It is a further object of the present disclosure to present a medical handling device that reduces distraction from the actual activity during operation/control, at least in certain embodiments.

It is a further object of the present disclosure to present a handling device, which optimizes the working conditions for the user/surgeon and helps the user to keep the overview, at least in certain embodiments.

SUMMARY

In regard of the medical handling device, these and other objects are achieved by a medical handling device, comprising:
an instrument holder for holding an observation instrument having an image capturing unit for capturing an image section,
a robotic handling unit that supports the instrument holder,
a control device with an instrument control unit for controlling the observation instrument and a handling control unit for controlling the robotic handling unit, and
an input device coupled to the control device for selecting an image section to be reproduced,
wherein the control device is adapted to control the robotic handling unit in response to user inputs at the input device to change the acquired image section, and
wherein the control device is adapted to convert direction commands at the input device into movement instructions depending on a present orientation of the image capturing unit, for instance into movement instructions for the robotic handling unit.

In this way, the object of the disclosure is completely achieved.

According to the invention, the embodiment of the control device ensures that the image section can be moved intuitively by the operator, independent of the (external) orientation of the observation instrument. This may have the potential advantage that the observation instrument and the robotic handling unit can be positioned favorably in relation to the patient, so that the remaining field of vision is not or only slightly disturbed.

The robotic handling unit can also be referred to as a telemedical handling unit. Even if it is basically conceivable to operate the handling unit fully or partially automatically, control by the operator/surgeon is provided for in exemplary embodiments.

This function can be used to move the selected image section, for instance in an imaginary plane. The input device can be used to enter control commands in the form of direction commands, which are then implemented by the control device so that the handling unit is controlled taking into account the concrete orientation of the image capturing unit. The user can move the image intuitively by converting direction commands at the input device, such as right, left, front and back, into corresponding translations/movements of the displayed image section. This simplifies the operation considerably. The risk of operating errors, which can have a major impact, for instance in the medical environment, can be reduced. The movement instructions are finally converted into control commands for drives of the axes of the robotic handling unit.

A motion input at the input device usually has a direction information and a travel information (amount). The movement instructions are control signals for controlling the robotic handling unit. The image section is the part of a scene that is selected for display. The image section comprises in exemplary embodiments a subset of a recording area of the image capturing unit.

In general, the input device can be used to manipulate the displayed image section via user inputs. This can include a movement (translation). However, a rotation as well as an enlargement/reduction (zoom and/or change of the image scale) is also conceivable. Furthermore, it is conceivable to control a focus drive for adjusting a focal plane (plane of focus) via the input device.

The input device can be used for controlling the observation instrument but also for controlling the robotic handling unit. This simplifies the operation for the operator considerably. It is not absolutely necessary to use two separate input devices.

It is also conceivable to mount other instruments as observation instruments on the instrument holder of the handling unit. Accordingly, the term instruments basically includes observation instruments, but also surgical instruments such as pliers, scissors, forceps, suction devices, etc.

The movement of the image section can be effected by the robotic handling unit, which actually moves the observation instrument with the image capturing unit. However, it is also conceivable to move the image section digitally. This is possible, for example, if an image capturing unit is used whose recording area is larger than the currently selected image section. In such a case, the captured area can be moved within the selected image section.

The instrument control unit can be referred to as CCU/controller/console. The input device for the manipulation (movement) of the image section in exemplary embodiments is connected to the instrument control unit via an interface. In other words, control commands for the handling control unit are transferred (in terms of signals) from the input device via the instrument control unit to the handling unit. Furthermore, the status of the image setting (zoom, focus, ROI position and image orientation) of the unit to be moved (e.g. exoscope) can be passed on to the handling unit via the CCU. The handling unit can then react accordingly, for example by changing the direction of movement when the orientation setting is changed, or by changing the pivoting radius when the focus setting is changed.

The control device can be distributed and thus comprise an instrument control unit for controlling the observation instrument and a separate handling control unit for controlling the robotic handling unit, which communicate with each other. It is to be understood that the distributed design can also be realized virtually (by software). Nevertheless, at least in exemplary embodiments, a hardware separation of instrument control unit and handling control unit is conceivable. In this way, the instrument control unit (CCU/console) remains universally usable, i.e. also for hand-held/hand-guided instruments.

In an exemplary embodiment, the input device is connected to the instrument control unit, wherein the instrument control unit is arranged—in terms of signals—between the input device and the handling control unit, i.e. therebetween. Furthermore, in this embodiment, the instrument control unit is arranged—in terms of signals—between the observation instrument and the input device. Signals are transmitted via the instrument control unit and/or, if necessary, even looped through.

In an exemplary embodiment, it is also provided that the input device (in the case of controlling an imaging parameter directly at the observation instrument) can be connected—in terms of signals—to the observation instrument via the robotic handling unit.

An aspect of present disclosure is based on the fact that the handling control unit controls the robotic handling unit depending on parameters of the observation instrument. This can for instance relate to parameters of an observation head/camera head of the observation instrument. For example, the handling control unit can control the travel speed of the links of the robotic handling unit as a function of a given magnification level (zoom factor, focus distance and/or object distance). For example, with a large zoom factor and/or a small object distance (corresponding to a detailed representation) the travel speed of the robotic handling unit can be reduced. Accordingly, the traversing speed of the robotic handling unit can be increased, for example, with a small zoom factor and/or a large object distance (corresponding to an overview display).

In a further exemplary embodiment, the handling device also comprises a display unit for displaying the captured image section, wherein the control device takes the present orientation of the image capturing unit into account when controlling the display unit for reproducing the image section. In other words, in an exemplary embodiment there is an artificial horizon and/or a specific coordinate system for the image capturing unit. This artificial horizon and/or specific coordinate system defines the position of the displayed image section on the display unit. The display device is for example a monitor, a screen, a projector, specific glasses for displaying (HMD—head-mounted display) or similar.

For instance with stereo image sensors for stereoscopic imaging or even for 3D imaging, the alignment is of high importance, so that the desired offset between the right and left image sensor is located in the correct plane. For that reason, even a stereoscopic image section cannot be rotated arbitrarily and continuously by software. Instead, in such a case a hardware rotation is regularly required to align the horizon.

According to a further exemplary embodiment of the handling device, the control device is adapted to detect a present orientation of the image capturing unit and, depending thereon, to perform a mapping between an input device coordinate system and a coordinate system of the handling unit, which reflects the orientation of the image capturing unit. Accordingly, the orientation describes the horizon and/or the rotational position of the image capturing unit.

In other words, it is conceivable, at least in some embodiments, that a right-left axis of the input device causes a right-left movement of the displayed image section. Similarly, a forward-back axis of the input device can cause a forward-back and/or up-down movement of the displayed image section. By way of example, the information relating to the current orientation of the image capturing unit is transmitted from the observation instrument to the control device.

The control of the robotic handling unit now takes place under the condition that the orientation of the image capturing unit is maintained. A corresponding interpolation of the movement over different axes of the handling unit contributes to the maintenance of this mapping.

According to another exemplary embodiment of the handling device, the observation instrument comprises an orientation sensor for detecting the orientation of the image capturing unit. In this way, the artificial horizon and/or the image capturing unit's own coordinate system can be detected, in terms of signals.

In a further exemplary embodiment, the detection of the present orientation of the image capturing unit is done indirectly via the display, in which the desired orientation (horizon position) is defined based on the displayed image section. It is also conceivable to detect the orientation of the image capturing unit indirectly via a controlling of a drive for rotation/turning of the image capturing unit. Accordingly, the orientation is not captured by a sensor, but is derived from the target specifications for the drive.

For instance with an image capturing unit with one observation channel (mono image sensor), a solely digital rotation and detection of the horizon is also conceivable.

According to another exemplary embodiment of the handling device, the image capturing unit in the observation instrument is rotatable. This relates for instance to an axis perpendicular to the image plane of the image capturing unit. Exemplary embodiments with stereo image capturing unit use such a function. It is basically conceivable to make the image capturing unit manually rotatable. However, it is also conceivable to provide a rotational drive/rotary drive for the image capturing unit. The rotatability of the image capturing unit allows for image erection.

According to another exemplary embodiment of the handling device, the control device is adapted to digitally rotate the image section that is captured by the image capturing unit. This is for instance conceivable with a mono image capturing unit with only one observation channel.

According to another exemplary embodiment of the handling device, the observation instrument comprises a stereo image capturing unit with at least two image sensors. In such a case, the image erection via the rotatability of the image capturing unit is potentially advantageous. In this way, the alignment of the observation channels with the human eye area can be achieved. Embodiments with more than two image sensors are also conceivable, e.g. if two sensors are assigned to a spectral range (visible light, infrared, etc.).

According to another exemplary embodiment of the handling device, the control device is adapted to map between the orientation of the image capturing unit and movement axes for input at the input device in such a way that directions of movement of the image section displayed by the display unit are brought into alignment with direction instructions at the input device. In this way, it is not necessary for the operator to make a notional alignment between the different coordinate systems/orientations. The operator can primarily use the displayed image section to move it in the desired way.

Accordingly, the implementation of the operating commands (direction commands and travel commands) by the control device includes a transformation of coordinates, which is taken into account in the control of the handling unit. The movement axes correspond, for example, to corresponding degrees of freedom of movement (forwards, backwards, right, left, etc.).

According to a further exemplary embodiment of the handling device, the control device is adapted to convert the movement instructions into control commands for movement axes of the robotic handling unit. In this way, a multi-axis handling unit can also be controlled in a simple way by operating the input device.

According to another exemplary embodiment of the handling device, the robotic handling unit comprises a multi-link kinematics with a plurality of coupling links, which are controlled by the handling control unit of the control device. This allows the observation instrument to be moved in a controlled manner with great freedom of movement in a given space. For example, the multi-link kinematics is a serial kinematics. It is to be noted that parallel or mixed serial-parallel kinematics can also be used.

According to another exemplary embodiment of the handling device, the input device is arranged as a multi-axis input device, for instance as a single-handed multi-axis input device, wherein the input device allows operating movements in the form of travel motions or pivot motions in at least two axes to capture movement signals for two-dimensional movement of the image section in one plane. The input device can be arranged as a so-called 3D mouse. By suitable action on the input device, for instance on an actuating element of the input device, a movement of the image section in the plane, for instance in an object plane and/or the recording area, can be controlled.

It is therefore conceivable to provide an input device with an input element that can be moved in different axes, wherein the movements (for example, translational movement along two or more axes, as well as rotational and/or pivot motion along two or more axes) are detected by suitable sensors and converted into control commands.

According to another exemplary embodiment of the handling device, the control device aligns the two movement axes of the input device with the present orientation of the image capturing unit, so that operating movements of an input element of the input device result in movements of the displayed image section in the same direction. This ensures that the operator can intuitively control the desired movements by moving left, right, up/front or down/back. The operator does not need to be concerned about the coordinate transformation. This is done by the control device.

According to another exemplary embodiment of the handling device, the input device is arranged as a single-handed input device, wherein the input device detects operating movements at least in the form of a rotation around a longitudinal axis or a translation along the longitudinal axis in order to detect movement signals for controlling a zoom function and for a focus adjustment. Accordingly, the input device can fulfill further functions. In a simple manner, a plurality of functions (movement, magnification, etc.) can be controlled in only one operating mode. However, it is also conceivable to provide different operating modes to allow unambiguous controlling.

As explained above, a zoom mode can include on the one hand a digital zoom. However, it is also conceivable that the zoom function (more precisely: change of the magnification scale) can be achieved by changing the object distance between the observation instrument and the object plane (optical zoom). In other words, the image capturing unit can be moved closer to the object to be observed. If the object distance is changed, it is necessary in at least some embodiments to adjust the focus as well. This is done, for example, by the focus drive.

In an exemplary embodiment, the input device comprises an input element, wherein a lift axis is provided, along which the input element can be moved in two directions and/or subjected to force. In addition, it is conceivable to design the input element to be rotatable about the lift axis. In this way, for example, a zoom function can be achieved by pushing and pulling the input element along the lift axis. It is also conceivable to control the focus drive by rotating the input element. Conversely, it is also conceivable to control the focus drive via the lift movement and the "zoom drive" (changing the magnification scale) via the rotary movement.

It is noted again that a change between the detailed display and the overview display can be achieved by a so-called digital zoom and additionally by changing the working distance between the observation instrument and the object plane via the robotic handling unit. In exemplary embodiments, both modes are provided, wherein the control device is adapted to enable a smooth "transition" between both modes. Ideally, the operator does not even notice whether there is a digital zoom or an image scale change by changing the object distance (working distance). Nevertheless, for the sake of simplicity, this is often generally referred to as zoom function.

It is understood that alternative embodiments are also conceivable, in which the observation instrument comprises an optical zoom, i.e. a lens with a variable focal length.

According to a further exemplary embodiment of the handling device, the handling control unit of the control device is adapted to move the displayed image section in response to operating commands at the input device via a movement of the robotic handling unit, and wherein the instrument control unit of the control device is adapted to move the displayed image section in response to operating commands at the input device via digital shifting of the displayed image section in a captured recording area. In this way, the (electronic) digital zoom and the zoom (more precisely: change of image scale) can be combined by moving the entire observation instrument via the handling unit.

The image section can therefore be moved in exemplary embodiments via the handling unit and alternatively via digital image shifting. The latter is the case if the displayed image section is smaller than the recording area. Both functions can be combined.

According to a further exemplary embodiment of the handling device, the input device is operable in a first operating mode for controlling the instrument and in a second operating mode for controlling the robotic handling unit, the handling device further comprising an enabling switch for activating the second operating mode, in which the robotic handling unit is movable in response to input commands at the input device.

In this way, a separation between functions where the handling unit is possibly or where it is definitely moved, and functions where the handling unit is not moved is possible. This increases safety. This is for instance the case when the operator controls the handling unit indirectly, and is guided by the displayed image and not necessarily by the actual movements of elements of the handling unit and the observation instrument.

Accordingly, it is conceivable in various embodiments to provide for an enabling switch for manipulation of the image section using the robotic handling unit, for instance in the event that the image section is moved via the robotic handling unit. This will ensure that the handling unit is not inadvertently moved.

According to a further exemplary embodiment of the handling device, the control device is adapted to perform an initialization procedure in order to acquire configuration information relating to the supported observation instrument, wherein the initialization for instance comprises a query via the instrument control unit, and wherein the configuration information is transmitted to the handling control unit and taken into account for the control of the handling unit.

In this way, the control device can determine what type of observation instrument is currently attached to the robotic handling unit, by way of example. The observation instrument type involves, for example, its dimensions, parameters of its image capturing unit, the ability to exchange data, a possible rotational position for turning the image capturing unit, and a possible sensor for detecting the rotational position of the image capturing unit, etc.

The term initialization procedure should not be understood to mean that it is merely a one-time procedure. The initialization procedure can be executed repeatedly, for example, for each specific treatment or diagnostic task, for example, when the control device is started up or when the handling device is changed. The initialization procedure can also be repeated in a targeted and automated manner, for example, by periodic repetitions. Conversely, it is conceivable that the operator can consciously trigger the initialization procedure.

In other words, during the initialization procedure a certain offset can be determined, wherein the control device (handling control unit) for the robotic handling unit uses this offset for controlling the robotic handling unit. This offset defines, for example, the position of the image capturing unit in relation to the elements of the handling unit. The offset may describe the geometric shape/extension/orientation of the observation instrument. In this way, the image capturing unit of the observation instrument can be precisely controlled to move the image section as desired.

By way of example, it is conceivable to start the query that is part of the initialization procedure by pressing the enabling switch. The initialization procedure can also be referred to as a setup procedure. Accordingly, it is conceivable to use different camera systems/observation instruments. The data (configuration information) can be provided directly by the observation instrument. Alternatively, the observation instrument can be identified by its ID, which can be used to query data from a database.

According to a further exemplary embodiment of the handling device, the control device is adapted to mirror the displayed image section upon request, wherein the implementation of operating commands at the input device takes the mirroring into account. In this way, a flip mode can be provided.

For example, a mirror image is created around a horizontal or vertical axis. This can happen, for example, when another operator takes over the control of the handling unit, who is standing on an opposite side of the patient from the view of the previously active operator.

According to a further exemplary embodiment of the handling device, the control device is adapted to control the handling unit in such a way that the observation instrument can be pivoted around a virtual pivot axis by interpolated movement of the handling unit, which is arranged parallel to the image capturing unit. In this way, an instrument with variable viewing direction can be "simulated". Instruments without an integrated swivel drive can thus also provide such a degree of freedom and/or function. It is understood that this function is for instance conceivable with instruments that are arranged outside the patient's body.

It is conceivable that in alternative embodiments, instruments with variable direction of view and corresponding (internal) drives are provided, wherein the control of the drives is also carried out via the input device. In this way, an intuitive controlling of the rotary actuator can take place.

According to a further exemplary embodiment of the handling device, the control device is adapted to operate the robotic handling unit in a direct control mode in order to move and align the observation instrument in space, wherein operating commands can be generated at the robotic handling unit by acting on an element of the handling unit adjacent to the instrument, and wherein the handling control unit is adapted to control the robotic handling unit in such a way that the observation instrument follows the induced movement, wherein the operating commands in the direct control mode are for instance provided via an operating element, which generates an enabling signal for the direct control mode via a sensor.

Such a direct control mode ("direct drag mode") can be used for instance for the rough positioning of the observation instrument in relation to the object field. If the robotic handling unit is controlled in a suitable way, a quasi-manual adjustment directly on the instrument holder or at least in the vicinity of the observation instrument is possible.

In such a mode, the instrument holder with the observation instrument mounted thereon can therefore be moved and aligned quasi-manually in space, wherein the control device is adapted to hold the robotic handling unit in the current position/orientation automatically, but to enable manual movement by direct gripping and moving It is conceivable to monitor the drives of the elements/links of the kinematic chain of the robotic handling unit in the direct control mode in such a way that the operating commands are detected. In this way, the aforementioned "tracking movement" can be generated. In other words, in the direct control mode, the robotic handling unit itself serves as an input device.

In this mode, it is not absolutely necessary from the point of view of the robotic handling unit to request extensive information relating to the observation instrument, since the movement is manually induced and controlled directly at the robotic handling unit.

In an exemplary refinement of this embodiment, an input device with an input element is provided to control the handling unit and thus the observation instrument in the direct control mode. The input device is placed directly on an element of the handling unit and for instance adjacent to the instrument holder and/or the mounted instrument. The input device and/or its input element itself can basically have a simple design. It may be a handle, which the operator can use to move/manipulate the handling unit by pulling, pushing or similar means.

In another exemplary embodiment, the input device for the direct control mode is equipped with a sensor that activates the direct control mode. Such a sensor can detect, for example, a touch or approach by a hand of the operator. In this way, the direct control mode can be enabled. In such a mode, the control device is adapted to detect operating movements of the operator and track the handling unit accordingly.

It is conceivable to provide sensors in the movement axes of the handling unit for this purpose. It is also conceivable, however, to monitor characteristic values/parameters of the movement axes, i.e. the drive motors, such as currents and the like, in order to be able to detect the control signals and consequently the movements induced externally by the operator. Alternatively, a sensor system is also conceivable, which only measures the spatial position of the front tip of the handling unit and/or the observation instrument itself, e.g. optical tracking system.

In regard of the control method, the above and other objects are achieved by a method for controlling a handling device, the handling device comprising a robotic handling unit with an instrument holder, and an observation instrument mounted thereon and having an image capturing unit for capturing an image section, the method comprising the steps of:

providing the observation instrument on the instrument holder, acquiring control commands for selecting an image section to be reproduced via an input device that is coupled to a control device for controlling the observation instrument and for controlling the robotic handling unit, and controlling the robotic handling unit in response to user inputs at the input device to change the captured image section, comprising:

converting direction commands at the input device into movement instructions, for instance movement instructions for the robotic handling unit, depending on the present orientation of the image capturing unit.

The object of the disclosure is also completely achieved in this way.

In other words, the transfer of direction commands involves a conversion between a coordinate system and/or "horizon" of the input device and a coordinate system and/or "horizon" of the observation instrument, for instance of its image sensor. Current orientations of the input device and the observation instrument (i.e. of its image sensor) are brought into alignment for control purposes. If this conversion is carried out by the system, the operator is spared a notional conversion during operation. The control of the handling device for shifting the image section is significantly simplified.

Changing the image section can be used to shift the displayed image section. This can be achieved by controlling the handling unit. Other manipulations of the image section are conceivable, such as rotation, tilting, combined movement and/or zoom in/out.

It is conceivable to use the method for controlling a medical handling device. It is conceivable to use the method for surgical and/or diagnostic processes. However, it is also conceivable to use the method for processes other than surgical and/or diagnostic processes. Consequently, exemplary embodiments, in which the method is not used to perform a surgical/diagnostic procedure on the human or animal body, are also conceivable.

It is to be noted that the control method can be further refined corresponding to the exemplary embodiments of the handling device and vice versa. In other words, the subject matter of exemplary embodiments and further refinements related to the handling device may also become the object of corresponding embodiments of the method described herein.

It is to be understood that the above-mentioned features of the invention and those to be explained in the following can be applied not only in the respectively specified combination, but also in other combinations or singly, without departing from the scope of the present invention.

BRIEF DESCRIPTION OF THE DRAWINGS

Further features and advantages of the invention are disclosed by the following description of a plurality of exemplary embodiments, with reference to the drawings, wherein:

FIG. 3 is a schematic, simplified partial view of an image capturing unit on an observation head of an observation instrument and a display unit to illustrate an image orientation;

FIG. 4 is another representation analogous to FIG. 3 with a corrected image orientation by rotating the image capturing unit;

EMBODIMENTS

Figure 1:
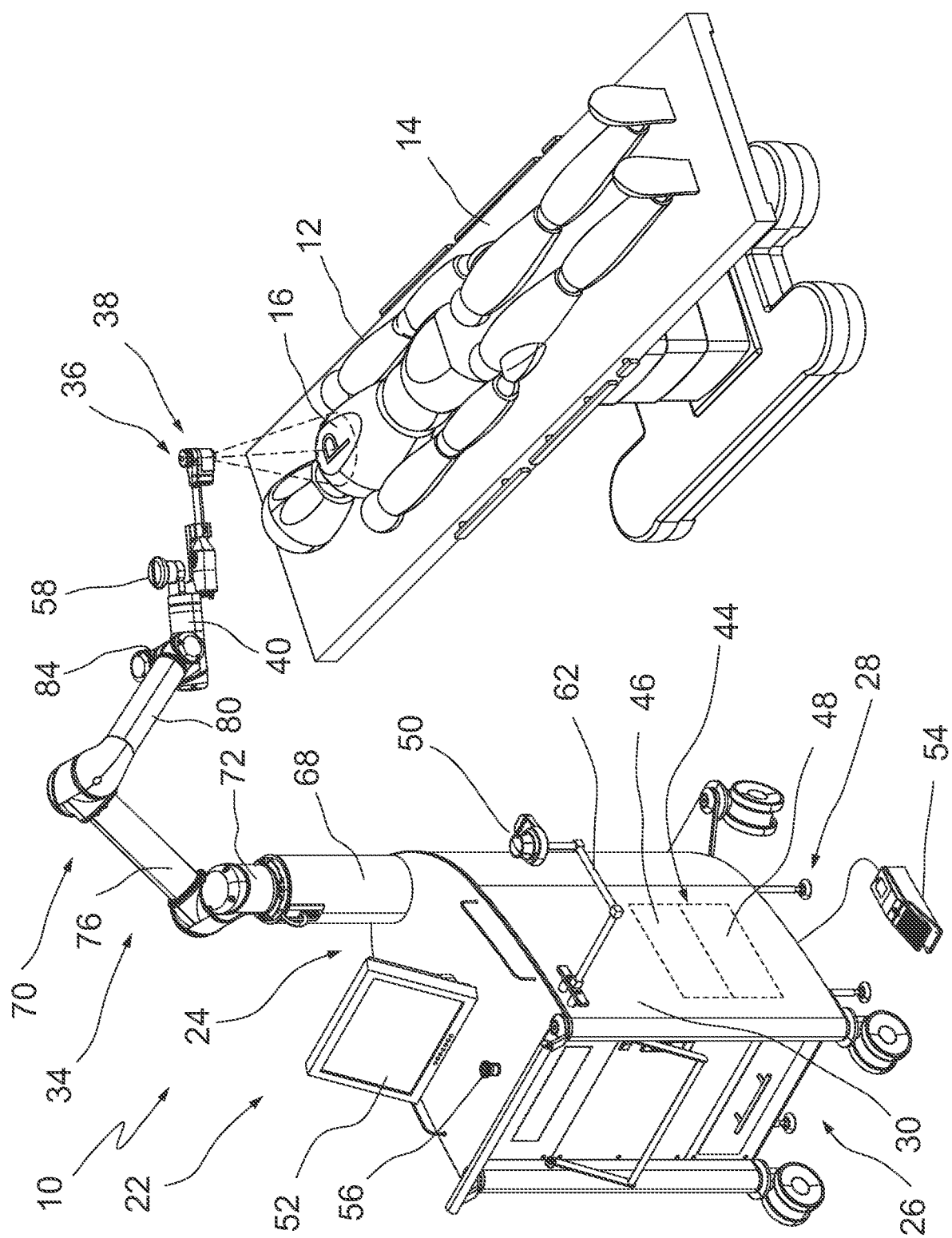
FIG. 1 is a perspective view of an embodiment of a medical handling device for observing an object field in a patient.

FIG. 1 shows a perspective overview of a handling device that is overall designated by 10. The handling device 10 can also be referred to as a medical handling device. In the embodiment shown in FIG. 1, the handling device 10 is assigned to a patient 12 who is placed on a table 14. The handling device 10 can be used for therapeutic, surgical and/or diagnostic purposes. However, its use for non-therapeutic, non-surgical and/or non-diagnostic purposes is also conceivable. This may include a use in exercises and/or simulations.

In the illustrated exemplary embodiment, the handling device 10 is used to observe an object field 16. The object field 16 is exemplarily a part of the patient's body 12. For illustrative purposes, the object field 16 is marked with the letter P in at least some of the figures shown herein. This is not to be understood to be limiting.

In the exemplary embodiment shown in FIG. 1, the object field 16 is located outside the body of patient 12. Accordingly, the handling device 10 in this exemplary embodiment serves to observe the body from outside the body. Alternative exemplary embodiments are conceivable, in which the handling device 10 can be used to observe the inside of the body, for example for endoscopic or laparoscopic observation.

In general, the handling device 10 is used for optical observation in the range of the visible electromagnetic spectrum and/or in adjacent peripheral areas. The main embodiments are therefore observations using white light, infrared radiation or UV radiation. Light that is visible to the human eye (white light) lies approximately in a spectral range between 380 nm and 780 nm. Radiation in the near-infrared range is in the range of about 780 nm to 1400 nm. So-called near UV light (also referred to as black light or UV-A light) is in the range of about 315 to 380 nm. So-called medium UV light (also referred to as UV-B light) is in the range of about 280 nm to 315 nm.

The above-mentioned areas can be used for white light observation as well as for PDD (photodynamic diagnostics) and PDT (photodynamic therapy) applications. This may also include fluorescence observation. In this context, fluorescence observation using indocyanine green (ICG) with fluorescence in the near infrared range is also conceivable.

The handling device 10 comprises a platform 22, which is arranged as a trolley or cart 24. This is not to be understood to be limiting. Nevertheless, at least in exemplary embodiments, a movable platform 22 is provided. This increases flexibility and suitability for various applications. Accordingly, the platform 22 is arranged as cart 24 with a chassis 26, for example. In the embodiment shown in FIG. 1, the cart 24 comprises not only a chassis 26 but also a so-called support 28 and/or a corresponding support unit.

The support 28 is used to protect the cart 24 against unintentional movement during operation of the handling device 10. Accordingly, the support 28 can be used to jack up the cart 24. As an alternative or in addition, it is intended to block the wheels of the chassis 26 in the sense of a parking brake. The status of the cart 24 (mobile or jacked up/locked) can be monitored by suitable sensors in order to enable operation of the handling device 10 only if it is ensured that the cart 24 cannot be moved unintentionally. It is understood that the cart 24 can also be anchored/fixed in other ways to enable safe operation of the handling device 10.

Furthermore, the platform 22 comprises a housing 30, which accommodates elements/units of the handling device 10. This results in a compact, clear design. In addition, the handling device 10 is easier to clean, and can also be arranged as a shelf or shelf trolley. In exemplary embodiments, essential control units for the handling device 10 are arranged in the housing 30 of the cart 24. This means that the platform 22 is mobile, so that use at different locations and/or in different rooms is conceivable. It is understood that the platform 22 and/or the cart 24 are nevertheless coupled with the environment, for example for energy supply, signal supply and/or media supply purposes.

The platform 22 or the cart 24 forming the platform supports a handling unit 34. In the illustrated exemplary embodiments, the handling unit 34 is arranged as a motorized handling unit, for example as a robotic handling unit. Alternatively, the handling unit 34 can be referred to as a telemanipulator unit. Accordingly, the platform 22 forms a base for the handling unit 34. At least in the embodiments shown herein, control devices for the handling unit 34 are located on the platform 22 and/or in its housing 30.

The handling unit 34 is adapted to carry/hold an instrument 36. The instrument 36 can be moved by motor via the handling unit 34. Accordingly, the handling unit 34 can be referred to as a telemanipulator for instrument 36. The instrument 36, for example, is a medical instrument. At least in exemplary embodiments the instrument 36 is arranged as observation instrument 38. The observation instrument 38 is, for example, an instrument for observing the patient from outside the body, i.e. at a distance from the patient's body. Such an observation instrument 38 can be arranged and referred to as an exoscope. However, it is also conceivable to design the observation instrument 38 as an instrument for observing the inside of the patient's body, for example as a laparoscope or endoscope.

The instrument 36 is mounted on an instrument holder 40. For instance, the instrument 36 is detachably mounted on the instrument holder 40. In other words, the instrument 36 can also be detached from the instrument holder and therefore from the handling unit 34. It is therefore conceivable to use the instrument 36 in alternative applications as a hand-guided/hand-held unit. For illustrative purposes, it is assumed in the following that the instrument 36 is used as an observation instrument 38 for observing an object field 16, for instance as a medical observation instrument 38 for observing an object field 16 in a patient 12.

In FIG. 1, the reference sign 44 illustrates a control device 44, which is mounted on platform 22, by means of dashed lines. By way of example, platform 22 comprises a cart 24 with a rack that includes an enclosure in the form of a housing 30. Accordingly, the control device 44 can be accommodated and held on this rack.

At least in exemplary embodiments, the control device 44 comprises a handling control unit 46 and an instrument control unit 48. The handling control unit 46 and the instrument control unit 48 can be discrete, basically separate control units/control modules. In other words, several units can be combined to form the control device 44. However, it is also conceivable to form the control device 44 in such a way that the handling control unit 46 and the instrument control unit 48 at least partially use common hardware/computer technology. In other words, it is conceivable to design the handling control units 46, 48 discretely and/or integrally. Mixed forms are conceivable.

For controlling the handling device 10 and, in certain embodiments, for interaction with the control device 44, various input devices are provided for an operator (e.g. a surgeon or an assistant). For example, an input device 50 is provided, which is arranged as a single-handed input device. For example, the input device 50 is arranged as a so-called 3D mouse, at least similar to a 3D mouse. In other words, the input device 50 can be adapted to detect user inputs and consequently control commands in several spatial axes, where the input is made by only one hand, acting on a single input element. The input device 50 is for instance used for controlling the robotic handling unit 34 as well as for controlling the observation instrument 38 and/or for controlling a reproduction of an image captured by the observation instrument 38. In this context, reference is again made to US 2017/0163972 A1, which discloses the use of a single-handed input device for controlling imaging parameters and for controlling image reproduction parameters.

Another input device 52 is arranged as a so-called touch monitor. Accordingly, the input device 52 can be used for selection decisions, general settings and similar functions. Basically, it is also possible to control the robotic handling unit 34 via the input device 52. The input device 52, arranged as a touch monitor, can be used, for example, to make general settings with regard to the instrument 36 (observation instrument 38). Furthermore, operating parameters for the operation of the observation instrument 38 can be selected and/or entered via the input device 52.

Another input device 54 is arranged as a foot switch, for instance. The footswitch can be operated by the operator without the need for hands. The input device 54 arranged as a foot switch can be used for instance as an enabling switch. The design as a foot switch is not to be understood to be limiting.

Basically, the input device 54 is intended to enable certain functions/operations when required, and only on the explicit command of the operator. In other words, the input device can be used to prevent certain functions from being triggered unconsciously. In this way, for instance the robotic handling unit 34 can be operated safely. This relates for instance to movements of the instrument holder 40 (with the instrument 36 mounted thereon) in relation to the patient 12 or the table 14. Such movements should be possible if there is an additional release signal via the input device 54. Furthermore, the input device 54, which serves as an enabling switch, can be coupled with a safety control (enable control).

Furthermore, the embodiment of the handling device 10 illustrated in FIG. 1 illustrates a further input device 56, which is arranged as a button or push-button. The input device 56 may basically be arranged as an emergency stop button. Accordingly, the input device 56 can cancel a current action of the handling device 10, for instance of the robotic handling unit 34. However, it is also conceivable that the input device 56, similar to the input device 54 described above, can be used as an enabling switch for activating (enabling) certain functions. Both embodiments increase the safety when operating the handling device 10.

In the embodiment of the handling device 10 illustrated in FIG. 1, a further input device 58 is provided directly on the robotic handling unit 34. The input device 58 is located on or near the instrument holder 40. The input device 58 is used in a so-called direct control mode for quasi-direct control/displacement of the handling unit 34 and consequently of the observation instrument 38. In other words, the operator can quasi-manually control the observation instrument 38 in the direct control mode (also referred to as direct drag mode) by simply dragging and/or pivoting/rotating the input device 58, which is designed, for example, like a handle, mushroom-shaped or button-shaped.

In the direct control mode, the handling unit 34 is operated by the control device 44 and/or by its handling control unit 46 in such a way that the robotic handling unit 34 immediately follows the operating commands. This gives the operator the impression that the observation instrument 38 can be maneuvered in space directly or almost directly. The handling unit 34 follows the movement, i.e. the control command, of the operator. If the control movement by the operator ends, the handling unit 34 remains in the currently selected position and holds this position and thus also the observation instrument 34 in space. In the direct control mode, the handling unit 34 can be controlled in such a way that a defined force must be overcome by the operator when directly acting on the input device 58.

In an exemplary embodiment, the input device 50 is connected to platform 22 via a boom 62. The boom 62 can have different links, which are adjustable. Therefore, depending on the situation, an ergonomically favorable position for the input device 50 can be set. For instance, the input devices 50, 52, 54, 56, 58 are directly or indirectly coupled to the control device 44 in terms of signaling (e.g. via data lines or radio). This can include a coupling with the handling control unit 46 and/or the instrument control unit 48.

Figure 2:
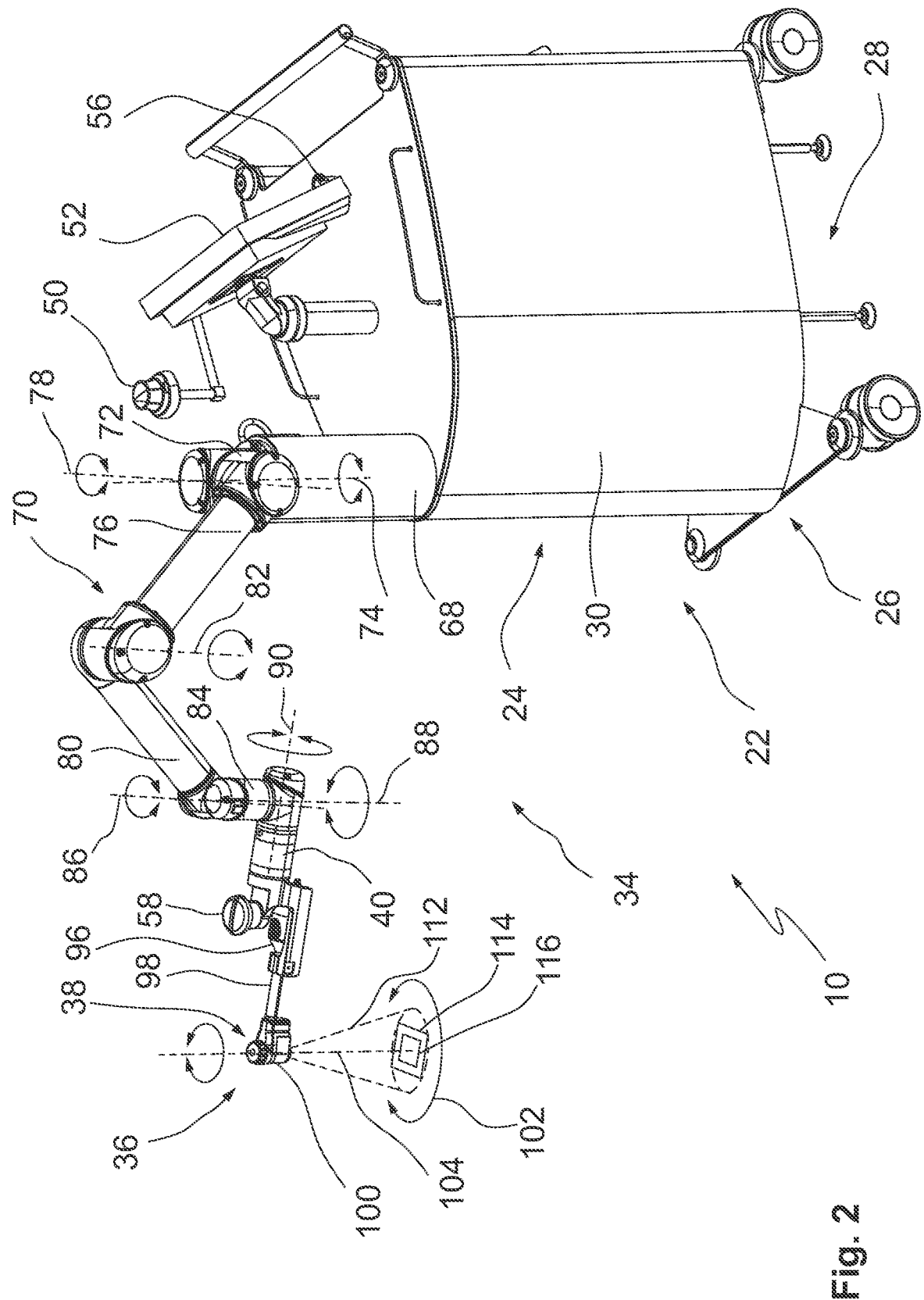
FIG. 2 is another perspective view of the handling device according to FIG. 1 in a different view orientation.

FIG. 1 and FIG. 2 illustrate an exemplary embodiment of the robotic handling unit 34. The handling unit 34 comprises a base frame 68, which is arranged on the platform 22, which is arranged as cart 24. In other words, the handling unit 34 can be moved at least in the exemplary embodiment shown in FIG. 1 and FIG. 2.

The handling unit 34 comprises a kinematic chain 70, the base of which is formed by the base frame 68 on the platform 22. The handling unit 34 is arranged as an open kinematic chain. In other words, the kinematic chain 70 comprises a number of links, which are arranged in a row and coupled to one another.

The handling unit 34 comprises a carousel 72, which is mounted on the base frame 68. The carousel 72 can be rotated (about a vertical axis) in relation to the base frame 68. Accordingly, a joint 74 is provided between the carousel 72 and the base frame 68. The joint 74 defines an axis of rotation (in the exemplary embodiment vertical axis). The base frame 68 forms a proximal end of the kinematic chain 70 of the handling device 34. The instrument holder 40 forms a distal end of the kinematic chain 70 of the handling device 34.

The carousel 72 is connected to a swing arm 76, which is coupled to the carousel 72 via a joint 78, cf. FIG. 2. The joint 78 defines an axis of rotation (in the exemplary embodiment horizontal axis). Furthermore an arm 80 is provided, which is coupled with the swing arm 76 via a joint 82. The joint 82 defines an axis of rotation. In the kinematic chain 70, an element referred to as hand 84 follows, which is coupled to the arm 80 via a joint 86 (cf. FIG. 2). The joint 86 defines an axis of rotation.

The element referred to as hand 84 is followed in the exemplary embodiment according to FIGS. 1 and 2 by the instrument holder 40 for supporting the observation instrument 38. The instrument holder 40 is coupled to the element referred to as hand 84 via a joint 88. Joint 88 defines a pivot axis. The instrument holder 40 can be rotated about the axis defined by joint 88 relative to the hand 84 and/or relative to the arm 80. It is also conceivable that the instrument holder 40 can be rotated about its longitudinal axis, cf. joint 90, which also defines a rotation axis. The illustration in FIG. 2 is not to be understood to be limiting.

In an exemplary embodiment, the joints 74, 78, 82, 86, 88, 90 are each assigned with a drive. The drive is for example a direct drive or servo drives. The drives are not explicitly shown in FIG. 2.

It is understood that the design of the handling unit 34 may also differ from the embodiment shown in FIGS. 1 and 2. This relates, for example, to the number of links in the kinematic chain 70 and/or the actual degrees of freedom and/or movement axes between adjacent links. Basically, the robotic handling unit 34 can be used to move the observation instrument 38 in at least two degrees of freedom relative to the patient 12 and/or the table 14. For instance, the handling unit 34 allows the observation instrument 38 to be moved in four, five, six or even seven degrees of freedom. It is to be noted that robotic handling units with more or less links and also with different degrees of freedom of movement may also be used. The number of movable (usually pivoting) axes is usually selected so that the desired degrees of freedom can be provided for the instrument 36.

FIGS. 3 and 4 illustrate by means of simplified schematic representations an exemplary embodiment of an observation head of the observation instrument 38, which is designated by 100, cf. also FIG. 2. The observation instrument 38 comprises a housing 96. A shaft 98 extends from the housing 96 towards a distal end of the observation instrument 38. The observation head 100 is located at the distal end. FIGS. 3 and 4 illustrate only the distal end of the observation instrument 38 with the processing head 100.

In FIG. 3 and FIG. 4, it can also be seen that at least in exemplary embodiments a rotational degree of freedom (cf. double arrow 102) is provided for the observation head 100 and/or for an image capturing unit installed therein. Accordingly, an image erection (image rotation) with respect to an optical axis 104 is possible, cf. also FIG. 2. The observation instrument 38 with the observation head 100 is adapted to observe a field of view 112 (cf. FIG. 2 and FIG. 5) and to capture an image section 116 in a recording area 114 in the field of view 112. This is done in an object plane and/or object field 16 (cf. FIG. 1). The field of view 112 is defined by an optical imaging system of the observation head 100.

The field of view 112 and image sensors (one or more sensors) installed in the observation head 100 define the (possible) recording area 114, which cannot be larger than the field of view 112. The recording area 114 is defined by the size of one or more image sensors and the imaging optics. The image section 116 can basically correspond to the recording area 114. However, it is also conceivable, at least in exemplary operating modes, that the image section 116 is deliberately chosen smaller than the recording area 114. On the one hand, this is conceivable for a digital zoom feature. Furthermore, the image section 116 can be selected smaller than the recording area 114 in order to avoid or at least minimize any imaging errors/display errors in the edge area of the recording area 114 (i.e. at the edges of the image sensors).

The observation instrument 38 comprises an image capturing unit 118 for capturing the image section 116 and/or the recording area 114. The embodiment shown in FIGS. 3 and 4 involves a stereo image capturing unit 118. Accordingly, the image capturing unit 118 comprises a first sensor 120 and a second sensor 122. The sensors 120, 122 are arranged as CCD image sensors, CMOS image sensors or similar. The sensors 120, 122 each have a plurality of detecting pixels. It is understood that the image capturing unit 118 can also be arranged as a (mono) image capturing unit with only one observation channel. The reference signs 124 each indicate a center and/or a center point of the sensors 120, 122.

A display unit 128 is provided for reproducing the captured image. The display unit 128 includes a monitor or a similar display. The display unit 128 is designed in exemplary embodiments for stereoscopic image reproduction. Accordingly, the display unit 128 can be arranged as a 3D monitor. Designs are conceivable, in which a monitor is viewed through auxiliary means (3D glasses) in order to achieve the stereoscopic effect. However, designs are also conceivable, in which the display unit 128 is arranged as a head-mounted display (HMD), for example as video glasses.

A stereo image capturing unit 118 enables stereoscopic observation, if necessary even 3D observation. This is made possible by an offset between the two sensors 120, 122, which is adapted to the offset between the right and left eye of the observer. In this way, a spatial impression is obtained during observation. However, stereoscopic observation requires that the two sensors 120, 122 are aligned in a certain way, namely along an (artificial) horizon 140, which is adapted to the position of the display unit 128 and indirectly to the position of the eyes and/or the eye area of the observer.

In the state illustrated in FIG. 3, the display unit 128 shows an image section 130 in a first orientation, which results from the orientation of the image capturing unit 118 in relation to the observation head 100 and, overall, from the orientation of the observation instrument 38 in relation to the object field 16 at the patient 12. The representation of the image section 130 in FIG. 3 illustrates an inclined orientation with reference to an example (letter P), in which the immediate understanding and for instance the assignment of directions is difficult for the observer. It would be desirable for the observer to use the orientation of image section 132 shown in FIG. 4. The orientation of the image section 130 in FIG. 3 results from the present orientation of the image capturing unit 118, cf. the horizon 140.

In order to align the displayed image section 132 in the desired way, it is necessary to rotate the image capturing unit 118 with the sensors 120, 122, cf. the orientation of the horizon 140 of the image capturing unit 118 in FIG. 4. For this purpose, the rotational degree of freedom 102 is provided, which enables image erection. The image erection using the rotatability of the image capturing unit 118 around the optical axis 104 with respect to the observation head 100 is in certain embodiments potentially advantageous for stereo image capturing units. However, there may also be benefits for mono image capturing units 118 with only one observation channel, for example with respect to given dimensions (for example an aspect ratio) of the image sensor used.

In an exemplary embodiment, the observation head 100 comprises a position sensor/orientation sensor 142 for detecting a rotational position of the image capturing unit 118 in relation to the observation head 100 and/or the shaft 98 of the observation instrument 38. Based thereon, a desired orientation of the image section 130, 132 can be set, depending on the actual orientation of the image capturing unit 118.

It is basically conceivable to manually rotate the image capturing unit 118 around its optical axis 104. In alternative embodiments, it is also conceivable to use a drive 144 to rotate the image capturing unit 118 around the optical axis 104. If a drive 144 is used, the orientation sensor 142 can be integrated into the drive 144. However, it is also conceivable to derive the rotational position/orientation of the image capturing unit 118 from control data for controlling the drive 144. Thus, if a certain rotational increment is given to the drive 144 for a rotational movement, then, conversely, at least the target orientation of the image capturing unit 118 is known.

It is understood that an electronic/digital image erection is also conceivable, wherein the image section that is captured and displayed is digitally rotated. However, such feature is hardly realizable in the case of stereo observation while maintaining the stereo functionality. However, in exemplary embodiments a digital fine adjustment or fine alignment is conceivable.

It is understood that, in principle, the observation instrument 38 could also be aligned via the robotic handling unit 34 in order to align the displayed image section 130, 132. However, this would often have the result that the observation instrument 38 and/or the handling unit 34 get in the way and could impair the free direct view of the operating field/object field for the surgeon and/or third parties. Furthermore, in many cases the operating field must be accessible for other instruments. For this reason, the robotic handling unit 34 is generally aligned in such a way that it disturbs the workflow as little as possible. In this case, however, the image capturing unit 118 may have to be rotated using the degree of freedom 102 in order to erect the image in the desired way.

However, this alignment/erection by rotation of the image capturing unit 118 may result in the robotic handling unit 34 not being able to be controlled intuitively. For example, if the observer/operator uses the input device 50 to give control commands in the form of direction commands and travel commands to move the observation instrument 38 via the handling unit 34, he regularly orients himself towards the displayed image section 116 (cf. Also reference signs 130, 132 in FIGS. 3 and 4). However, the orientation of the scene in image section 116 often does not correlate with the actuation axes (for example right-left-front-back) of the input device 50. In such a case, a movement to the right at the input device 50 does not necessarily lead to a corresponding movement of the displayed image section 116 to the right.

FIG. 3 and FIG. 4 further illustrate an exemplary embodiment where the displayed image and/or the displayed image section 116, 132 is smaller than the theoretically available recording range 114 of the sensors 120, 122. Thus, if only a section of the respective recording area 114 is displayed, it is theoretically possible to displace the displayed image section 116 within the recording area 114. This is indicated in FIG. 4 by a shifted image section 134 and a coordinate system marked 136. Furthermore, this allows, as already indicated before, a so-called digital zoom, at least within certain limits.

The orientation of the image section 114 in FIG. 3 (in relation to the image section 116, 130 displayed by the display unit 128) illustrates that a larger image section 114 is also potentially advantageous for digital image rotation. Thus, the displayed image section 116, 130 can be rotated at the given aspect ratio and/or generally at the given shape of the display unit 128 without omissions in the corners of the display unit 128, for example.

The ability to select the image section 116, 132 smaller than the recording area 114 leads to situations where a current center and/or center of the displayed image section 116, 132 does not correspond to the center 124 of the sensor 120, 122. This must be taken into account when operating the handling device 10.

In accordance with an aspect of the present disclosure, it is proposed to interpose a coordinate transformation in order to allow intuitive control of the handling unit 34 for the movement of instrument 36 and/or observation instrument 38. This approach makes it possible, for example, to use the displayed image section 116 as a basis for controlling, for instance its orientation.

Figure 5:
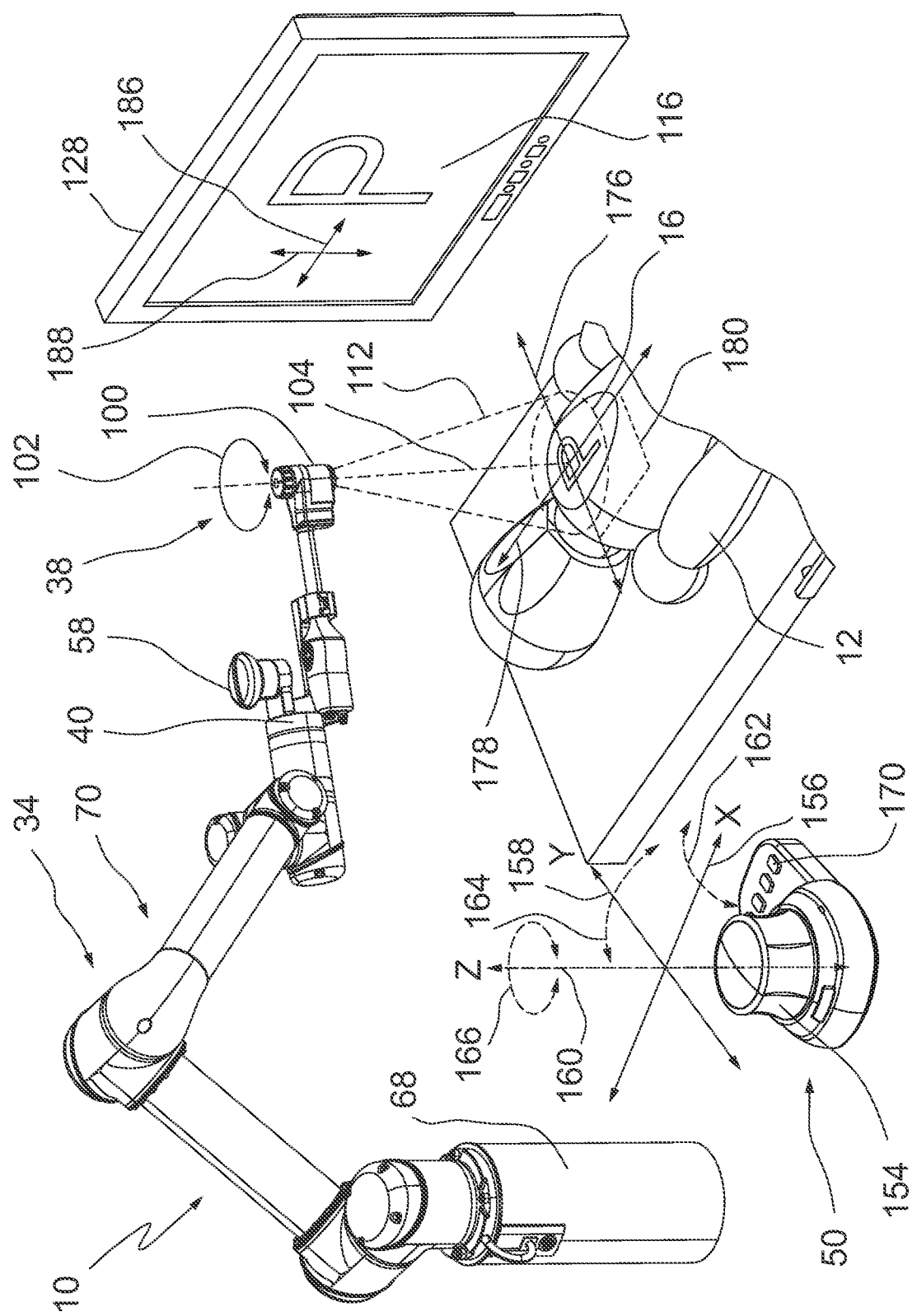
FIG. 5 is a partial perspective view of an embodiment of a handling device with an observation instrument to illustrate an exemplary function of the handling device.

This is illustrated with additional reference to FIG. 5. FIG. 5 shows a state, in which the image capturing unit (not explicitly shown) in the observation head 100 of the observation instrument 38 is aligned around the optical axis 104 in such a way that the image section 116 shown in the display unit 128 is shown in the desired orientation. This orientation is now the basis for controlling the robotic handling unit 34.

The control of the handling unit 34 is carried out, for example, via an actuating element 154 of the input device 50. By way of example, the actuating element 154 is designed button-like, plate-like or puck-like. However, the actuating element 154 can also be designed similar to a joystick. Alternatively, the actuating element 154 can be designed similar to a so-called rotary pushbutton. The actuating element 154 comprises different movement axes and/or input axes. Control commands can be generated via these input axes by the operator acting on the actuating element 154 in the desired way. For instance, the actuating element 154 is arranged as a multi-axis actuating element. Accordingly, the actuating element 154 is designed, for example, to detect movements along several linear axes 156, 158, 160. A total of six degrees of freedom are conceivable, for instance three translational and three rotational degrees of freedom.

By way of example, the axis 156 can be referred to as a translation axis. The axis 156 is exemplarily assigned to an X-direction. A travel motion/linear movement can be induced along the axis 156. It is understood that the actuating element 154 can only be deflected to a small extent along the axis 156. By way of example, the axis 158 can be referred to as a translation axis. The axis 158 is assigned to a Y direction, by way of example. A travel motion/linear movement can be induced along the axis 158. It is understood that the actuating element 154 can only be deflected to a small extent along the axis 158. By way of example, the axis 160 can be referred to as a lift axis. The axis 160 is assigned to a Z direction, by way of example. A travel motion/linear movement can be induced along the axis 160. It is understood that the actuating element 154 may only be deflected to a small extent along the axis 160.

In other words, translational movements of the observation head 100 of the observation instrument 38 in a plane (approximately an X-Y plane) can be caused by slight movements of the actuating element 154 along the axes 156, 158.

The lift axis 160 can be used, for example, to change an object distance (reference mark 196 in FIG. 6 and FIG. 7) between the observation instrument 38 and the object field 16. Basically, it is also conceivable to use a movement along the lift axis 160 (Z direction) for controlling a focus drive.

In addition, the actuating element 154 according to the embodiment as shown in FIG. 5 comprises pivot axes and/or rotation axes 162, 164, 166. The pivot axis 162 describes pivot motions around the axis 156, for example around the X-axis. The pivot axis 164 describes pivot motions about axis 158, for example about the Y-axis. The pivot axis or rotation axis 166 describes pivot motions/rotational movements about axis 160, for example, about the Z-axis.

The pivot axes 162, 164 can be used, for example, to tilt observation instrument 38, which is mounted on the robotic handling unit 34, with respect to the object field 16. This is done by controlling the handling unit 34 in reaction to pivot motions about the pivot axes 162, 164, which the operator performs on the actuating element 154. In an exemplary embodiment, the observation instrument 38 is pivoted around the focus point, i.e. the set working distance (pivot motion).

The rotation axis 166 can be used, for example, to control a focus drive of the observation instrument 38. Basically, it is also conceivable to change the working distance/object distance (reference sign 196 in FIG. 6 and FIG. 7) between the observation instrument 38 and the object field 16 in response to user inputs (rotational movements). It is possible to switch between these operating types by using an enabling switch. By way of example, axis 160 is used for changing the working distance and axis 166 for controlling the focus drive. Conversely, it is conceivable to use axis 160 for controlling the focus drive and axis 166 for changing the working distance.

In principle, it is conceivable to form the actuating element 154 to be deflectable in several spatial directions. In this way, a clear operation is achieved for the operator. However, it is also conceivable to detect the effect of a force on the actuating element 154, for example by means of suitable force sensors. In such a case, the actuating element 154 is not necessarily macroscopically deflectable. Instead, it has a microscopic deflectability. In this way, movements can also be detected and assigned to axes 156, 158, 160, 162, 164, 166 and, on this basis, converted into control commands.

The input device 50 has, for example, further actuating elements 170 in the form of buttons or knobs. In this way, further functions can be controlled. For instance, certain commands can be acknowledged. Furthermore, a selection of a current operating mode of the input device 50 via one of the actuating elements 170 is conceivable. Another possible use for the actuating elements is a storing of current positions of the handling unit 34 and/or the observation instrument 38, wherein the stored position can be approached from a position that has been assumed in the meantime. Both the storing of a position and the moving to a previously stored position can be effected by the operating elements 170. Moving to the previously stored position can be limited to the target position. Alternatively, the previously stored position can be approached in such a way that the previously used movement path is traversed "backwards".

In accordance with the example configuration illustrated in FIG. 5, a coordinate transformation and/or an alignment of the orientations/coordinate systems is performed to simplify controlling.

In FIG. 5, double arrows 176, 178 that are projected into the object field 16 illustrate a coordinate system that reflects the orientation of the image capturing unit. Accordingly, in the operating mode shown in FIG. 5, it is desired to move the observation instrument 38 and consequently the object field 16 in a plane 180 in response to operating commands at the input device 50. Such a movement in the plane 180 is achieved by interpolation and corresponding controlling of the links of the kinematic chain 70 of the robotic handling unit 34.

In the image section 116 shown on the display unit 128, the resulting movement axes 186, 188 are indicated. In the illustrated exemplary operating mode, axis 156 at the input device 50 is assigned to the resulting axis 186. Furthermore, the axis 158 at input device 50 is assigned to the resulting axis 188 in image section 116. Accordingly, the robotic handling unit 34 is controlled in such a way that the displayed image section 116 is moved to the right or to the left when the input element 154 is moved to the right or to the left. Furthermore, the robotic handling unit 34 is controlled in such a way that the displayed image section 116 is moved up or down along the indicated axis 188 when the input element 154 is moved back and forth. Such an operation is intuitive and can be carried out while observing the displayed image section 116 on the display unit 128.

However, this operating mode requires the detection of a current orientation (curved double arrow 102) of the image capturing unit in the observation head 100 and a consideration of this alignment (cf. double arrows 176, 178) in the control of the robotic handling unit 34, for instance when using a stereo image capturing unit 118 (cf. FIG. 2 and FIG. 3). In FIG. 5, for example, the horizon 140 of the image capturing unit 118 (cf. again FIG. 2 and FIG. 3, also cf. the double arrow 176 in FIG. 5) is aligned parallel to the interpolated axis 176. This alignment is taken into account when interpolating the trajectories for the desired X-Y movements in the plane 180. In other words, when implementing operating commands at the input device 50, the coordinate transformation is for instance carried out in such a way that axes 156, 176, 186 are aligned parallel to each other in respect of the control commands to the handling unit 34, and that axes 158, 178, 188 are aligned parallel to each other in respect of the control commands to the handling unit 34. Then, the displayed image section 116 can be easily moved in the 180 plane.

The operator can therefore orientate himself independently of the external orientation/position of the handling unit 34 and/or the observation instrument 38 by the orientation of the image section 116 on the display of the display unit 128, in order to control the image section 116 intuitively in at least two axes via user inputs on the assigned input axes 156, 158 of the input device 50.

At least in exemplary embodiments, other degrees of freedom of the actuating element 154 of the input device 50 are not taken into account during this specific travel mode, so that an ideal or almost ideal movement in plane 180 is possible.

Of course, other modes of operation are also conceivable, such as a spatial mode or 3D mode, in which the input device 50 can be used to control/move the observation instrument 38 in three or more spatial axes (translation axes/linear axes and pivot axes/rotation axes).

FIG. 5 illustrates a mode, in which the observation instrument 38 is moved as parallel as possible with a constant distance to the observed object field 16. The object distance (cf. again the reference sign 196 in FIG. 6 and FIG. 7) remains essentially the same.

Figure 6:
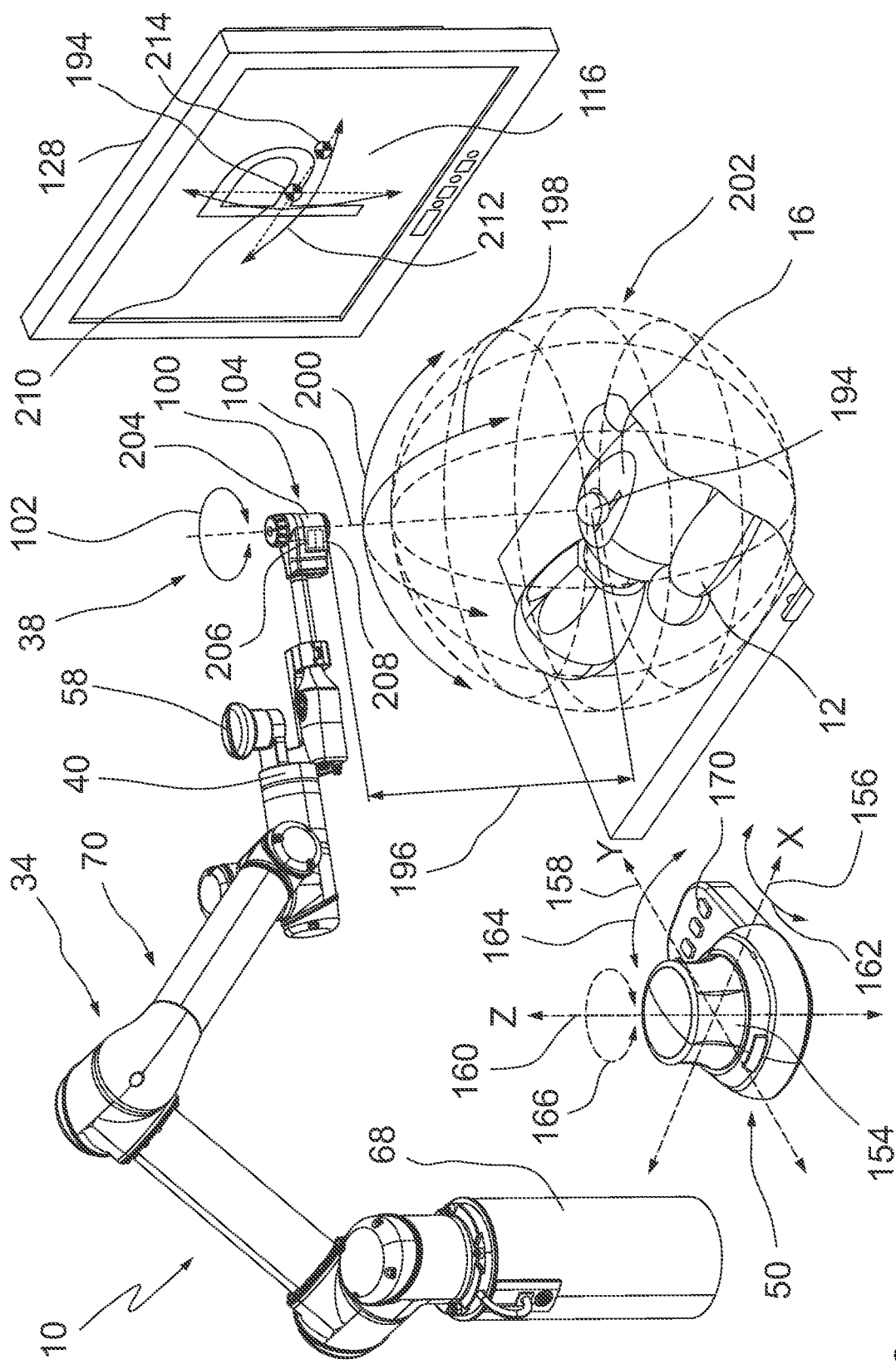
FIG. 6 is another partial perspective view of an embodiment of a handling device with an observation instrument to illustrate another exemplary function.

In addition, FIG. 6 illustrates another mode, in which the observation instrument 38 is moved along a curved path or surface/shell with respect to a pivot point 194 in the object field 16. By way of example, the pivot point 194 is a center of the image section 116, which represents a part of the object field 16. The movement along the curved shell (for example a spherical shell or a spherical half shell) is carried out at least in exemplary embodiments under consideration of a constant object distance 196.

In other words, the movement of the observation instrument 38 can be along interpolated curved axes 198, 200, which are assigned to a spherical surface 202 (sphere or spherical segment). By way of example, and not to be understood to be limiting, the axis 198 is associated with a 0° longitude and the axis 200 with a 90° longitude. The movement along/on the spherical surface 202 is performed while maintaining an alignment with the optical axis 104 to the selected pivot point 194, which can be derived from a current center of the observed image section 116. However, the pivot point 194 can also be located and selected off-center in the image section 116. The pivot point 194 can basically also be referred to as a focus point.

In an exemplary embodiment, the observation instrument 38 comprises observation optics 204 at observation head 100. By way of example, a focus drive 206 is assigned to the observation optics 204 for focus adjustment. The focus drive 206 is used to adjust a focus distance of the observation optics 204 to the selected working distance/object distance 196 so that the currently observed object field 16 is imaged sufficiently sharply. The focus drive 206 can be controlled manually and/or automatically.

At least in exemplary embodiments, the observation instrument 38 also comprises a measuring device 208 for determining the object distance 196. In this way, the current object distance 196 can be determined. During the movement of the observation instrument 38 along the curved path and/or surface 202 illustrated in FIG. 6, the object distance 196 is to be kept constant. For this, however, the object distance 196 must first be determined, at least in some of the embodiments. This is done by the measuring device 208.

In an alternative embodiment, the control device 44 may determine the object distance 196 indirectly via current operating parameters of the observation optics 204 and/or the focus drive 206. In other words, a certain state of the observation optics 204 indicates a certain object distance 196.

By way of example, controlling the movement along the curved axes 198, 200 is done using the pivot axes 162, 164 of the input device 50. In other words, for example, pivoting the actuating element 154 about the X-axis 156 (pivot axis 162) can control a movement along the curved axis 198. For example, a rotation of actuating element 154 about the Y-axis 158 (pivot axis 164) can control movement along the curved axis 200. In FIG. 6, resulting movements of the displayed image section 116 on the display unit 128 are indicated by curved double arrows 210, 212. It is understood that the display unit 128 usually comprises a flat screen. Therefore, the arrows 210, 212 are curved for illustration purposes only.

In other words, the mode of the handling device 10 shown in FIG. 6 allows the observation instrument 38 to orbit around the center of the image section 116, while the observation instrument 38 remains aligned with the center with its optical axis 104. Similar to a planet, the observation instrument 38 can orbit the center, while the optical axis 104 remains radially aligned with the center.

Again, it is noted that for instance for a stereo image capturing unit 118 (FIG. 3 and FIG. 4), the present alignment of the image capturing unit 118 (horizon 140) is determined and is taken into account in controlling by means of coordinate transformation, so that the operator can intuitively orientate himself on the displayed image section 116. Control pulses that are detected using the pivot axes 162, 164 lead to movements of the displayed image section 116 in the same direction along the resulting axes/paths 210, 212. Operation is significantly simplified.

It is basically conceivable to locate pivot point 194 also in the center of the displayed image section 116. This may be accompanied by the pivot point 194 eventually also coinciding with the center 124 of the sensor 120, 122 of the image capturing unit 118 (cf. FIG. 3). In this way, a double central alignment is provided.

As explained above in connection with FIG. 4, there may also be situations where the center of the displayed image section 116 does not coincide with the center 124 of sensor 120, 122. In such a case, it is still conceivable that the pivot point 194 in the center of the displayed image section 116 is selected. Accordingly, there is an offset between the pivot point 194 and the actual center 124 of the sensor 120, 122. This offset is taken into account by the control device 44, for instance by the handling control device 46, in the movement control of the observation instrument 38 along the curved path 198, 200. Nevertheless, the goal of the control is to keep the selected pivot point 194 in the center of the displayed image section 116.

However, it is also conceivable that a pivot point 214 is chosen, which is deliberately not in the center of the displayed image section 116. There is an offset between the center of the displayed image section 116 and the selected off-center pivot point 214. Thus, an off-center anchor point is mentally chosen as the center of the movement of the observation instrument on the curved surface 202. The control device 44, for instance the handling control device 46, can be adapted to maintain this offset, which is present on the display of the display unit 128, during movement. In other words, in this mode, the optical axis 104 of the observation instrument 38 is deliberately not aligned with the center of rotation, i.e. the off-center pivot point 214.

It is understood that the operating modes shown in FIG. 5 and FIG. 6 can be combined if the operator moves the actuating element 154 both translatorily (axes 156, 158) and rotationally (axes 162, 164). However, it is also conceivable to separate the two operating modes. Accordingly, there is a parallel shift mode, a pivot mode and a combined mode. The corresponding modes can be selected, for example, via the actuating elements 170 on the input device 50 or otherwise.

Figure 7:
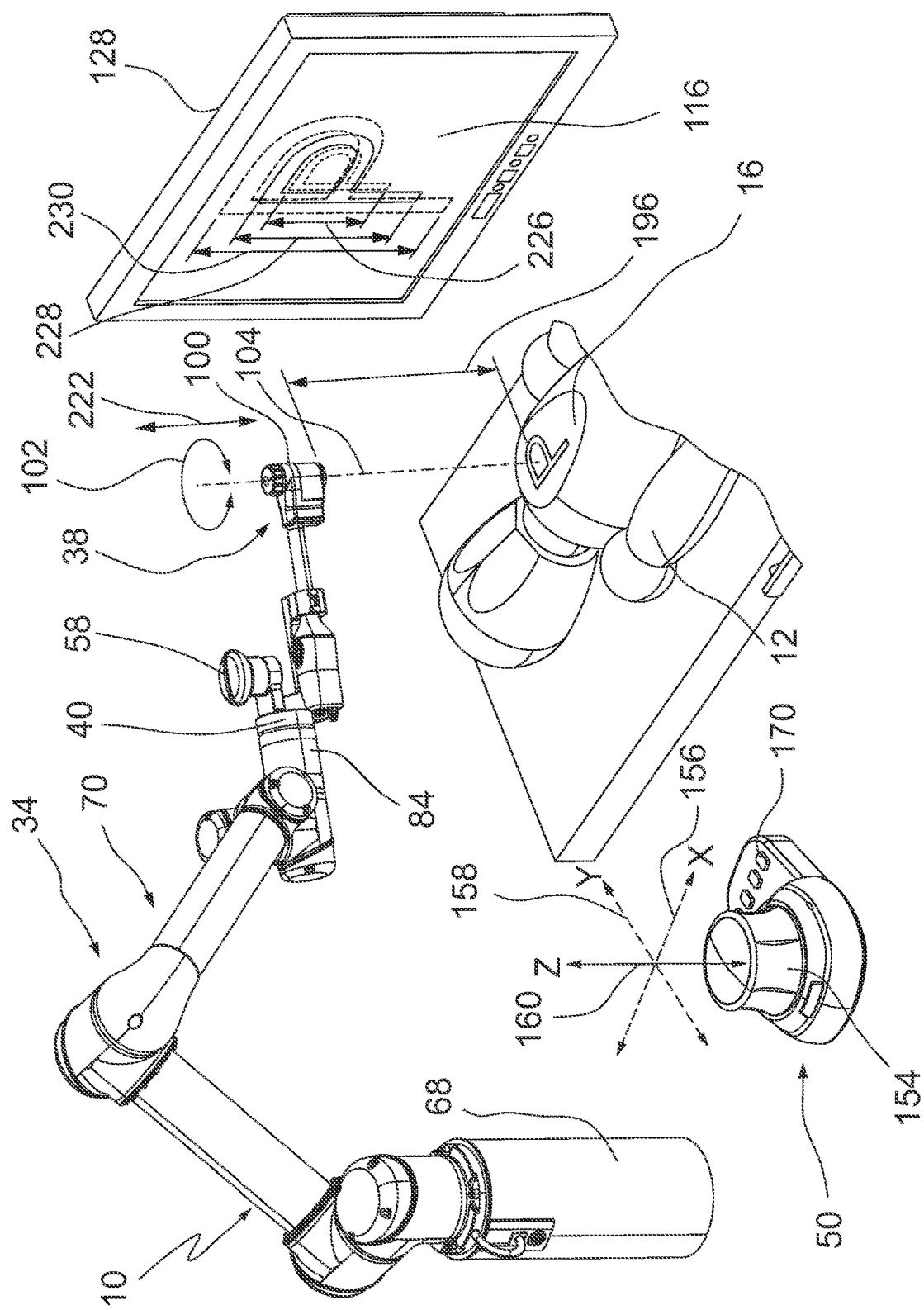
FIG. 7 is another partial perspective view of an embodiment of a handling device with an observation instrument to illustrate another exemplary function.

FIG. 7 illustrates the use of the input device 50 for controlling further functions of the optical observation instrument 38. By way of example, the lift axis 160 of the input device 50 can be used to induce a change in the object distance 196, cf. the interpolated axis 222. Using this function, an enlargement (detail increase) and/or increase in the magnification scale can be effected when the observation head 100 with the image capturing unit 118 moves closer to the object level/object field 16.

The result of a change of the working distance/object distance 196 is illustrated by the double arrows 226, 228, 230 in the displayed image section 116. When the working distance is decreased, the displayed image appears larger. When the working distance is increased, the displayed image appears smaller. In this way, a zoom function can be achieved—at least in terms of the result. This can be achieved by manipulating the actuating element 154. This can include pushing or pulling along the lift axis 160 (Z-axis). However, it is also conceivable to achieve this function by rotating the actuating element 154 about the Z-axis 160 (rotation axis 166).

At least in exemplary embodiments it is necessary to adjust the object distance of the optical unit of the observation head 100 so that the image appears sharp at the selected object distance. Here, again, one of the degrees of freedom of movement (cf. axes 160, 166) of the actuating element 154 of the input device 50 can be used to control a focus drive.

In alternative embodiments, an optical unit with variable focal length is integrated in the observation head 100, so that an optical zoom can be realized. In alternative embodiments, a so-called digital zoom is possible at least within limits. This is for instance the case when the reproduced image section 116 is smaller than the theoretically possible recording area 114 of the image capturing unit and/or smaller than the field of view of the optical unit. In this case, the captured and/or reproduced image section 116 can be varied at least slightly within the limits defined by the recording area 114, in order to enable an enlarged detail display or reduced overview display.

Furthermore, it is conceivable to couple the digital zoom with alternative measures for providing enlarged/reduced image sections in order to enable intuitive controlling of such an enlargement function via one and the same input device 50. The mode, in which the input device 50 is used to change the object distance 196 by moving the observation instrument 38 along the interpolated axis 222, can in principle be used simultaneously with the modes described in FIG. 5 and FIG. 6. However, it is also conceivable to separate the individual modes from each other in order to enable unambiguous operation.

Furthermore, in an exemplary embodiment it is conceivable to select a travel speed of the robotic handling unit and consequently of the observation instrument 38 mounted thereon dependent on a selected zoom level and/or as a function of a selected working distance/object distance 196. Accordingly, the observation instrument 38 can be moved more slowly if an enlarged display (high zoom factor, small object distance and/or large image scale) is selected. In this way, the changing image section 116 can still be captured well for the observer. Conversely, the observation instrument 38 can be moved faster if a reduced display (small zoom factor, large object distance and/or small image scale) is selected. This is possible because the displayed image section 116 covers a larger area of the object field 16.

Figure 8:
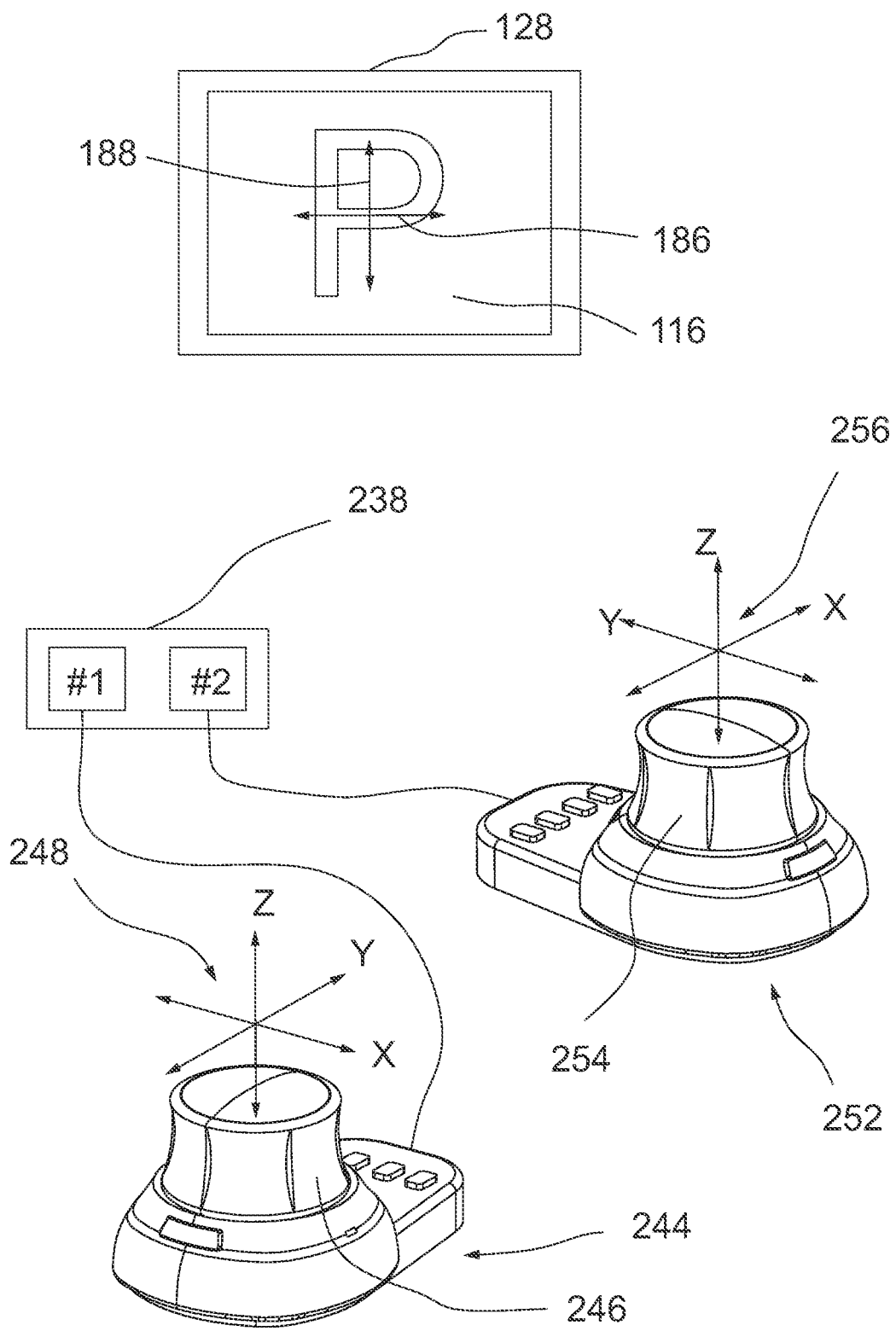
FIG. 8 is a schematic view of an arrangement comprising two input devices, which can be used for control purposes in the handling device.

FIG. 8 illustrates in conjunction with FIG. 1 that a plurality of input devices 244, 252 can be coupled via an interface 238 with the control device 44, i.e. the handling control unit 46 or the instrument control unit 48. In FIG. 8, the input devices 244, 252 are each single-handed input devices with an input element 246, 254, which can be operated in various room axes to generate control commands. Cf. the coordinate systems 248, 256 assigned to the input devices 246, 254. A plurality of input devices 244, 252 may be required to enable manipulations by different operators in the operating environment. On the one hand, this may involve controlling the robotic handling unit 34. It may also involve controlling the observation instrument 38, e.g. for controlling imaging parameters and/or image reproduction parameters.

It is understood that the control device 44 with the interface 238 uses a suitable activation/prioritization/hierarchy to define in a clear way, which of the input devices 244, 252 is currently used. In this way, for example, a primary input device 244 and a secondary input device 252 may be defined, wherein the primary input device 244 has a higher priority. Accordingly, the secondary input device 252 is deactivated and/or its commands are ignored if the primary input device 244 is used. Other measures for defining the currently used input device are conceivable.

The medical handling device 10 can basically be controlled via different types of input devices, cf. the input devices 50, 52, 54, 56 and 58 in FIG. 1. FIG. 8 shows two input devices 244, 252 of the same type. However, this is not to be understood as to be limiting.

Regardless of the current position and orientation of the input devices 244, 252, their users can orient themselves by the current image section 116 of the display unit 128 when controlling the robotic handling unit 34. In other words, the coordinate systems 248, 256 of the input devices 244, 252 are brought into alignment with the resulting movement axes 186, 188 of the displayed image section 116.

It is also conceivable to provide different display units 128, for example different monitors or HMDs for different users. This may include situations where users use different orientations (rotational orientation) of the displayed image section 116 on their assigned display unit. Then the respective input device 244, 252 and/or its coordinate system 248, 256 can be brought into alignment with the respective orientation of the image section in order to be able to move the image section intuitively. This can simplify the operation for different operators. For instance, in the medical domain it is conceivable that different persons are involved in a medical procedure. Accordingly, it is conceivable that the responsibility for operating the handling device 10 and/or the robotic handling unit 34 could be changed between those involved in the temporal sequence of a medical procedure.

Figure 9:
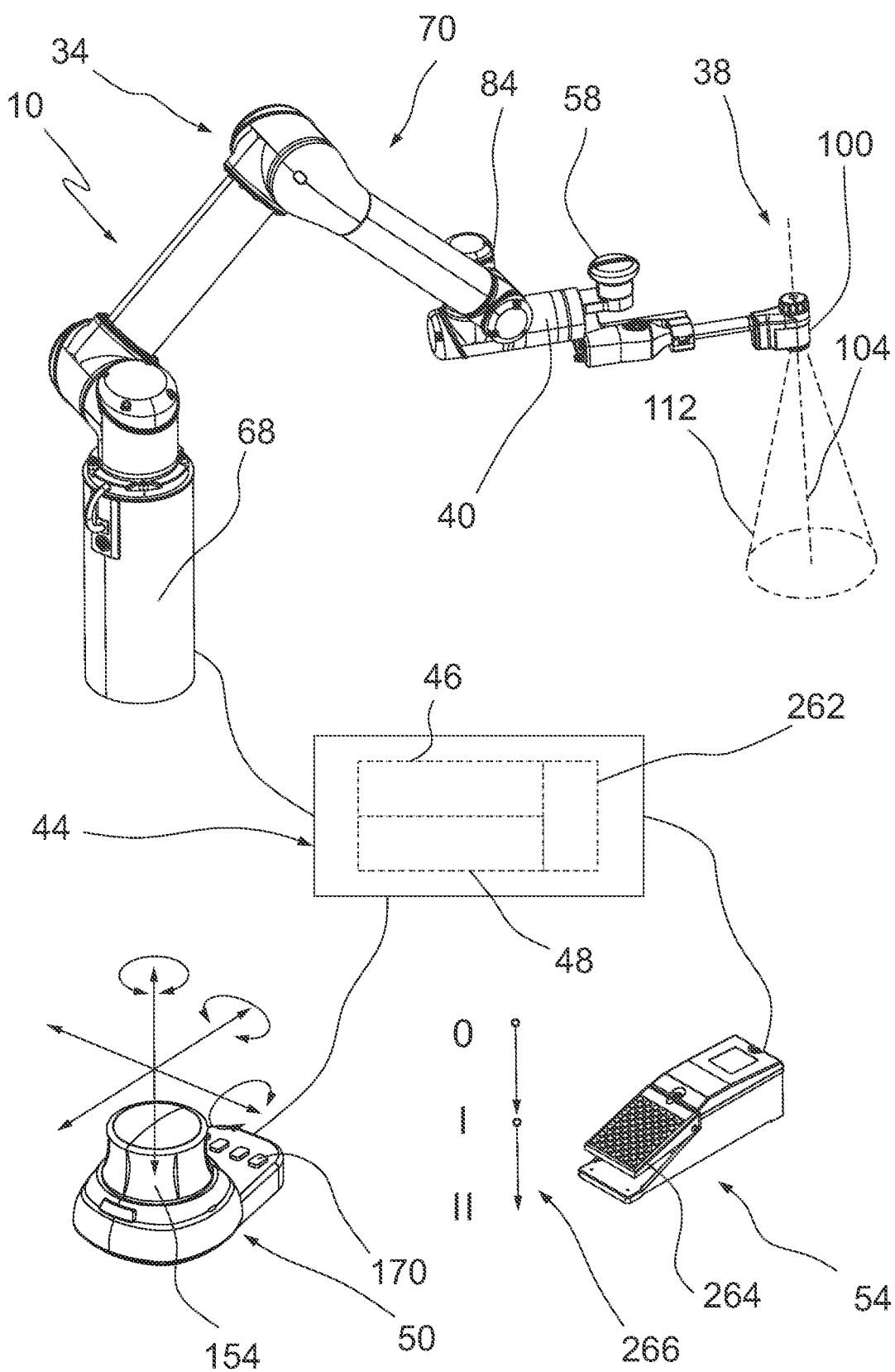
FIG. 9 is a perspective, simplified partial view of an embodiment of a handling device having an input element that acts as an enabling switch.

In conjunction with FIG. 1, FIG. 9 illustrates a release process for increasing safety when operating the handling device 10, for instance the robotic handling unit 34. For this purpose, a safety device 262 is provided, which may also be referred to as an enable control. The safety device 262 can be arranged as a component of the control device 44, cf. the schematic representation of the control device 44 with the handling control unit 46 and the instrument control unit 48 in FIG. 9.

The input device 50 can be used to control the robotic handling unit 34 so that links of the kinematic chain 70 are moved to move the observation instrument 38. This can have considerable consequences in case of errors or operating errors. Accordingly, in exemplary embodiments, an additional release process using an enabling switch is provided. An example of an enabling switch is the input device 54 and/or its input element 264. The input element 264 is arranged as a foot switch, for example. The enabling switch has a double function, since it enables the movement of the robotic handling unit 34, and it can also be used to switch back and forth between the control of the observation unit 38 and the robotic handling unit 34.

It is to be noted that the input device 56 (cf. FIG. 1), which is arranged on the platform 22, can also be used as an enabling switch. Accordingly, the safety device 262 can be configured in such a way that controlling the handling unit 34 is only possible if a corresponding mode is activated via the input device 54.

The safety device 262 ensures that only deliberate manipulation of the current position of the observation instrument 38 is possible. Operating errors/unconscious operations can be avoided.

In exemplary embodiments, the input device 54 is hard-wired to the safety device 262. In other words, the safety device 262 can be a discrete safety device, which is not only implemented by software in the control device 44. In this way, the safety device 262 is designed independently. This makes manipulations more difficult. A fixed coupling of the input device 54 (hard-wired) makes manipulation of the input device 54 more difficult.

The input device 54 and/or its input element 264 has/have at least two switch positions. A first switching position (stage 0) corresponds to an unactuated state, for example. In this state, the input device 50 cannot be used to control and move the handling unit 34. A second switch position (stage I) can cause a state, in which the input device 50 is activated, so that commands at the input device 50 are processed by the control device 44 to control and move the handling unit 34.

To further increase safety, at least in exemplary embodiments a third stage (stage II) is provided, which can also be referred to as panic mode/panic stage. The second stage (stage I) is provided for this embodiment between the first stage (stage 0) and the third stage (stage II). In other words, the operator must apply a certain minimum force to move the input element 264 of the enabling switch from the first stage (deactivation state) to the second stage (activation state). However, this actuating force must not exceed a defined maximum force. If the maximum force is exceeded, input element 264 of the enabling switch is moved from the second stage (activation state) to the third stage (deactivation state or panic state). A defined actuating force must therefore be applied, which lies in a range between a minimum force and a maximum force, in order to be able to control the robotic handling unit 34 via the input device 50.

This arrangement further increases safety. Namely, if the enabling switch in the form of the input device 54 is unintentionally actuated with high force, the input device 50 is not necessarily enabled for operating commands. Instead, the activation state/enabled state (second stage and/or stage I) is passed through and/or skipped and the input device 54 is set to the third stage (stage II).

It is understood that the enabling switch may also be configured differently. For example, it is conceivable to deliberately operate the enabling switch with only a first stage (stage 0) and a second stage (stage I). Other actuating elements may be provided, such as additional operating elements, which must be actuated together with the enabling switch. In the embodiment shown in FIG. 9 the enabling switch is arranged as input device 54 in the form of a foot switch. It is understood that also manually operated switches can be used as enabling switches.

Figure 10:
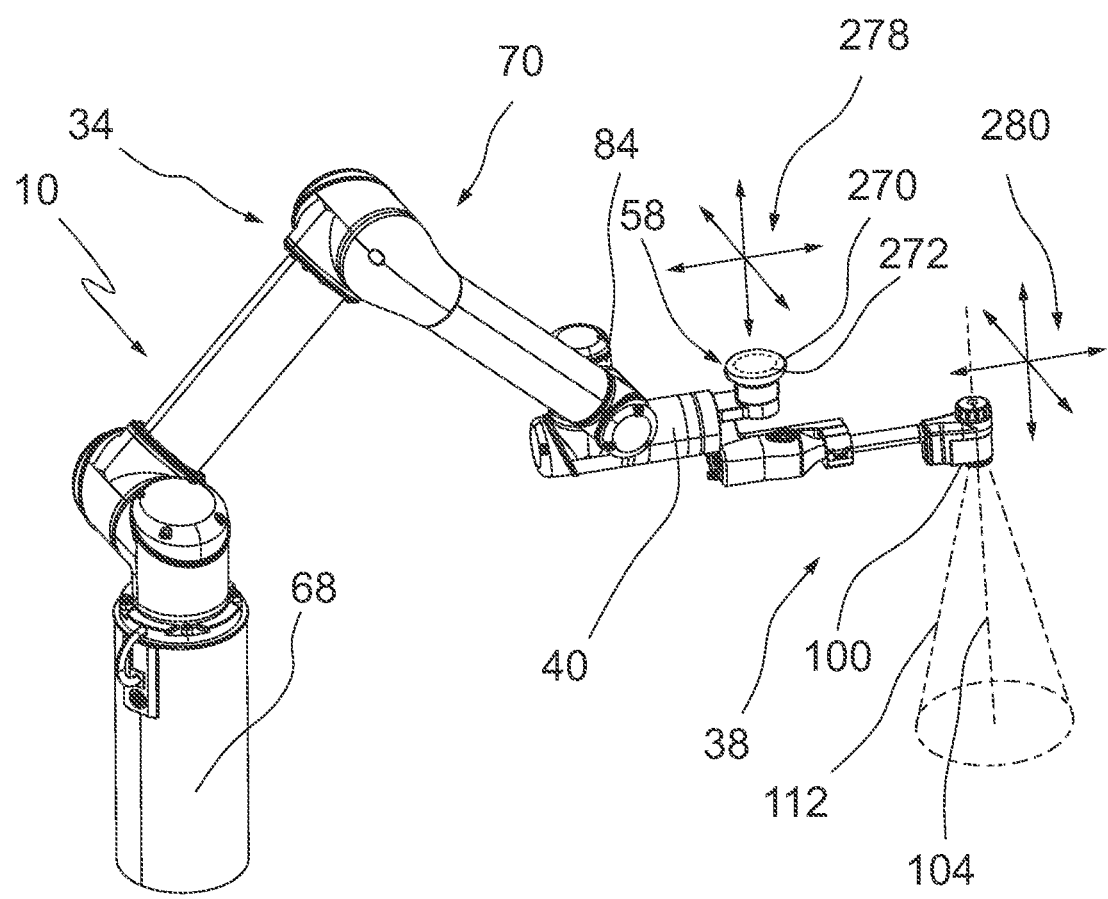
FIG. 10 is an additional perspective partial view of an embodiment of a handling device with an observation instrument to illustrate another exemplary function.
Figure 10:
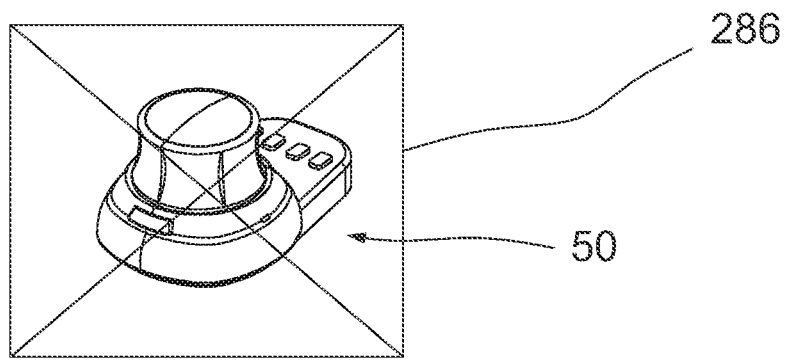

FIG. 10 illustrates another exemplary operating mode of the handling device 10, for instance the handling unit 34. The operating mode illustrated in FIG. 10 can also be referred to as direct control mode. In the direct control mode, the robotic handling unit 34 is not controlled via the input device 50, cf. the crossed-out block marked 286 in FIG. 10.

Instead, in the direct control mode, the control of the handling unit 34 is carried out directly by a manipulation and/or an engagement on an element of the kinematic chain 70 of the handling unit 34. For this purpose, in the embodiment shown in FIG. 10 there is provided the input device 58, which comprises an input element 270 in the form of a handle or knob. The operator can grasp the input device 270 and move it in space. The input device 58 with the input element 270 is exemplarily arranged on the instrument holder 40 of the robotic handling unit 34, i.e. in the immediate vicinity of the supported observation instrument 38. The input device 58 can also be referred to as a direct control input device.

At least in an exemplary embodiment, the input device 58 at the input element 270 comprises a sensor 272, which detects, for example, an approach or presence of the operator's hand. In this way, the control of the handling unit 34 can be enabled via the input device 58 in the direct control mode.

It is conceivable to dispense with an additional release for the release of the direct control mode using a sensor 272 in input element 270 of the input device 58 (cf. the input device 54 that is used as enabling switch in FIG. 1 and FIG. 9). This is conceivable because the operator can directly, or almost directly, influence the position and orientation of the observation instrument 38 mounted on the instrument holder 40 via the input device 58. In such a case, the operation is clearly and directly possible.

In the direct control mode, force and travel impulses applied by the operator to the input element 270 of the input device 58 are detected and evaluated by the handling control unit 46 (cf. FIG. 1), wherein drives of the elements of the robotic handling unit 34 are controlled in such a way that the robotic handling unit 34 with the instrument holder 40 and the observation instrument 38 mounted thereon follows the induced movement at the input device 58. It is to be noted that in the direct control mode both translational movements and rotary movements/pivot motions of the observation instrument 38 mounted on the handling unit 34 can be effected.

The acquisition of the operating impulses can be done by monitoring the various axle drives of the kinematic chain 70 of the handling unit 34. The operating impulses can be sensed in the axle drives and can therefore be detected. Alternatively, corresponding sensors can be assigned to the axle drives.

Alternatively or additionally, it is conceivable to provide the input device 58, similar to the input device 50, with its own degrees of freedom of movement and corresponding sensors to detect deflections. It is also conceivable to provide force/deformation sensors for the input device 58 and/or its input element 270 to record how the operator wants to move the handling unit 34 with the observation instrument 38.

In the direct control mode, the control device 44, for instance the handling control unit 46, controls the handling unit 34 in such a way that it follows the movement impulses of the operator at the direct control input device 58, and that the current position and/or orientation is maintained when the operator no longer acts on the input device 58. In this way, the operator can move the observation instrument 38 quasi-manually, involving direct and immediate feedback.

In FIG. 10, an input coordinate system 278 is assigned to the input element 270 of the input device 58. A coordinate system 280 that is aligned therewith illustrates the resulting interpolated movement for moving the observation instrument 38 via operating impulses at the input device 58. The observation instrument 38 follows the operating impulses at the input device 58 directly due to the proximity between the input device and the observation instrument 38.

The handling control unit 46 can be operated in such a way that the operator feels a certain, but not too great resistance (braking torque) in the direct control mode when operating the input device 58. This allows sensitive movement and position setting in the direct control mode.

It is also conceivable to use the control device 44 in the direct control mode, for instance its handling control unit 46, to record the movement path of the handling device 34 manually controlled by the operator via the input device 58 and to run it "backwards" if necessary. In this way, the control device 44, for instance its handling control unit 46, can provide a return function. The device can therefore move to the start position or another position that has been stored, starting from the current position. This is also possible in other control modes, not only in the direct control mode. For example, the storage and recall of selected functions can be controlled via the actuating elements 170 on the input device 50 or via other actuating elements.

Figure 11:
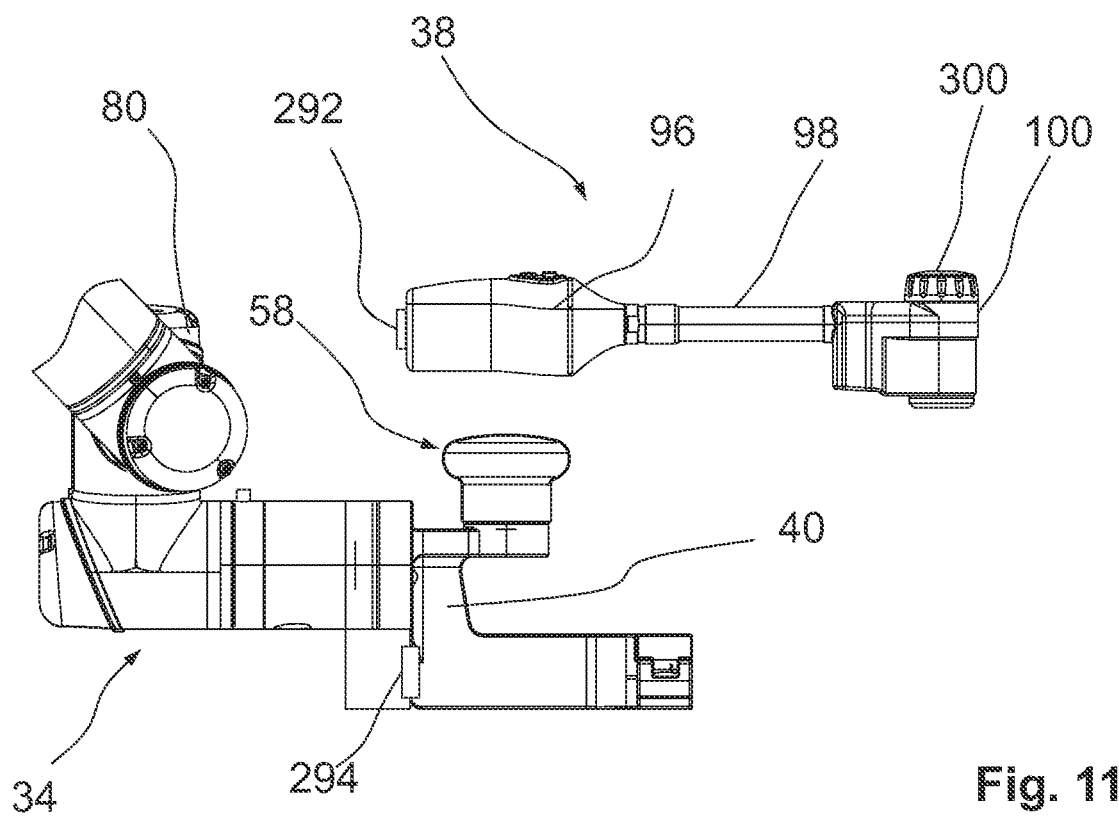
FIG. 11 is a side view of an instrument holder with an observational instrument that can be mounted thereon, in an unmounted state.
Figure 12:
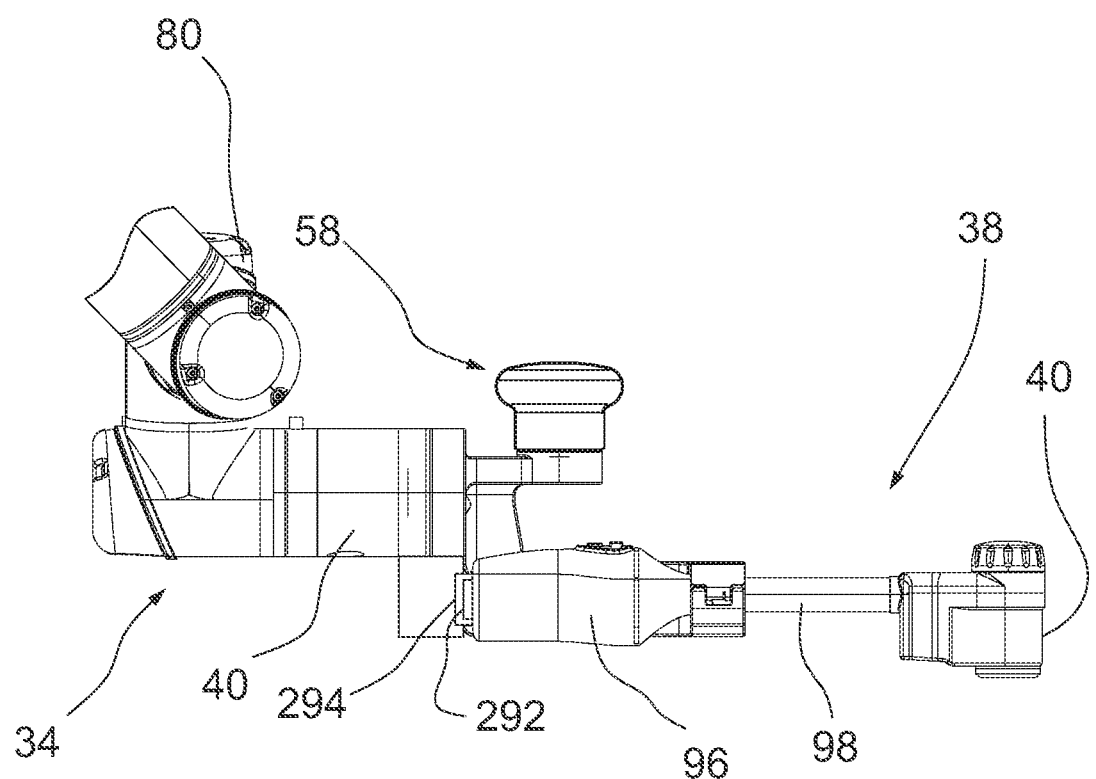
FIG. 12 is another view of the arrangement according to FIG. 12 in a mounted state.

FIGS. 11 and 12 illustrate the attachment of the observation instrument 38 to the instrument holder 40 of the handling unit 34. In FIG. 11, the observation instrument 38 is detached from the instrument holder 40. In FIG. 12, the observation instrument 38 is attached to the instrument holder 40. In addition to the mechanical coupling between the observation instrument 38 and the instrument holder 40, a coupling—in terms of signaling—via interfaces 292, 294 is also provided. An interface of the observation instrument is designated by 292. An interface on the part of the handling unit 34 is designated by 294. Accordingly, together with the mechanical coupling, a coupling in terms of signaling may also take place.

In connection with the attachment of the observation instrument 38, the control device 44 of the handling device 10 can therefore determine via the interfaces 292, 294, which type of instrument the observation instrument 38 is. Such an identification can be used for an instrument type-specific basic setting (parameter set) of the handling unit 34. By way of example, this can involve taking into account the present dimensions of the observation instrument when controlling the robotic handling unit 34. Furthermore, it is conceivable to exchange information relating to a rotary drive 300 for the image capturing unit (not explicitly shown in FIGS. 11 and 12) on observation head 100 via interfaces 292, 294. Furthermore, it is conceivable to obtain information relating to a current orientation/rotational position of the image capturing unit.

Via the interfaces 292, 294, image information can be transmitted, e.g. image signals of the monitored image section and/or recording area. In addition, information is transmitted, which can be used for the operation of the robotic handling unit 34.

It is conceivable that the observation instrument 38 contains identification information (ID), which can be requested via interface 292, 294. Accordingly, the control device 44 could then request a parameter set relating to the observation instrument 38 on the basis of this information, e.g. in a database. It is also conceivable that the observation instrument 38 itself could provide this information via interface 292, 294.

The arrangement illustrated in FIGS. 11 and 12 relates to the exchange of information between the observation instrument 38 and, on the one hand, the handling control unit 46 and, on the other hand, the instrument control unit 48. Respective signals/information are transmitted via the interposed handling unit 34.

Figure 13:
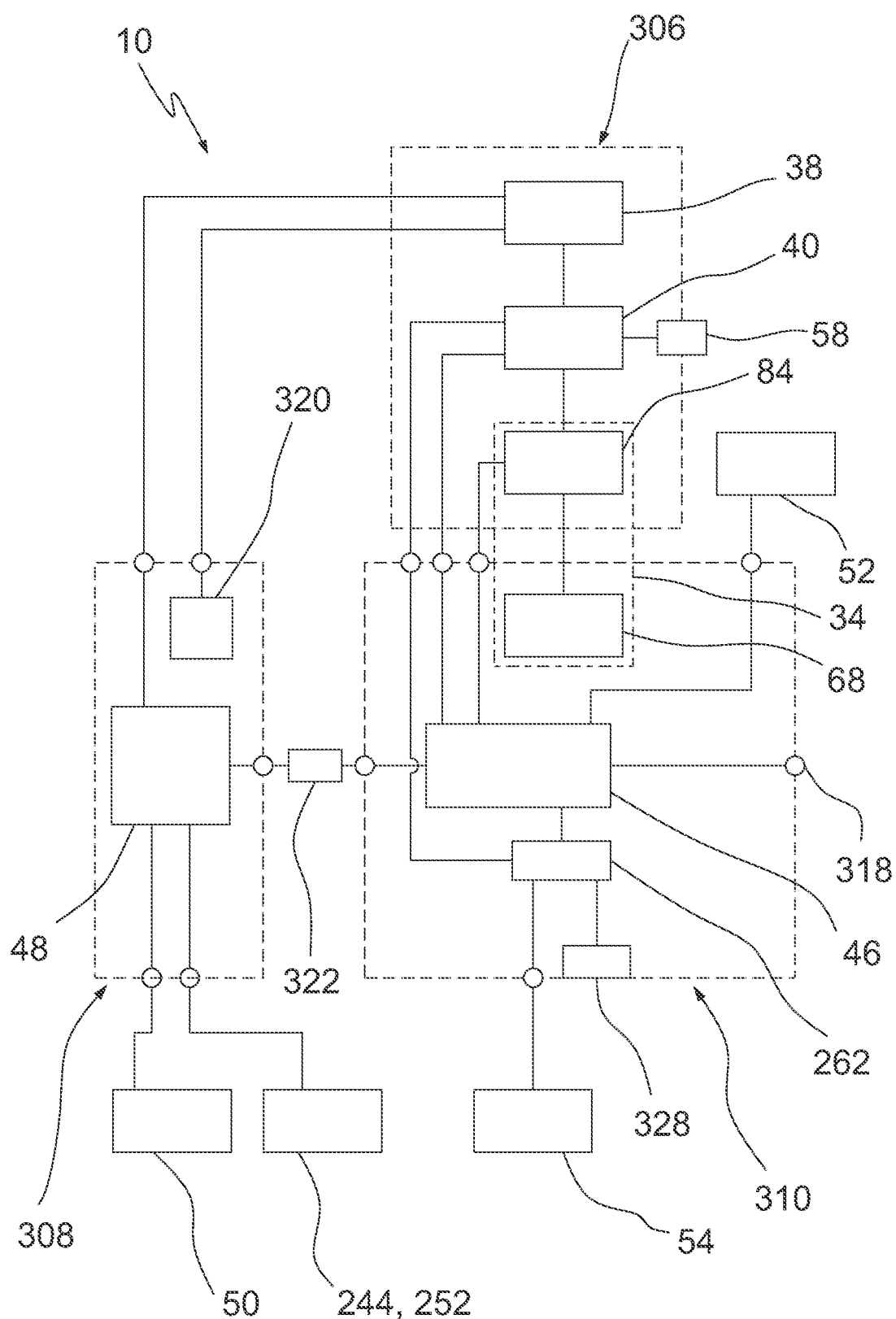
FIG. 13 is a schematic block diagram to illustrate a principle design of an embodiment of a handling device.

FIG. 13 illustrates with reference to a schematic representation a block diagram to illustrate an exemplary functional arrangement/system architecture of a handling device 10. From a structural point of view, the handling device 10 shown in FIG. 10 can basically correspond to the design of the handling device 10 illustrated in FIGS. 1 to 12.

The handling device 10 comprises an observation section 306, an instrument control section 308 and a handling section 310. The sections 306, 308, 310 are functionally separate sections. They are not necessarily structurally separate sections. The observation section 306 comprises the observation instrument 38 mounted on the holder 40. Furthermore, input device 58 for the direct control mode is assigned to observation section 306. By way of example, the input device 58 comprises a sensor for activating the direct control mode.

A mechanical connection between observation section 306 and handling section 310 is provided via the robotic handling unit 34, which is equipped with the hand 84, for example, which supports the instrument holder 40, cf. FIG. 2. The handling unit 34 also comprises a base and/or frame 68, which is assigned to handling section 310. The handling section 310 also includes the handling control unit 46 for controlling the handling unit 34. The handling unit 46 is provided with an interface 318 for power supply. The interface 318 can also be used for information exchange and/or media supply.

In addition, the handling section 310 is also assigned—in terms of structure—with the input device 52, which is arranged as a touch monitor, by way of example. The input device 52 is coupled with the handling control unit 46 and therefore also with the (global) control device 44. The handling section 310 also includes the safety device 262, which can also be referred to as an enable control. By way of example, the safety device 262 is coupled with the input device 54, which is arranged as an enabling switch. By way of example, in terms of signaling, the safety device 262 is coupled to the handling control unit 46 in order to enable or block operating modes of the handling control unit 46 and, consequently, of the handling unit 34.

In the exemplary embodiment shown in FIG. 13, safety device 262 is also coupled with a locking sensor 328, which monitors whether platform 22 supporting the handling unit 34 and/or cart 24 is braked and secured. At least in exemplary embodiments, this is also a condition for releasing the movement of the handling unit 34.

The instrument control section 308 basically involves the instrument control unit 48, i.e. the CCU/console for monitoring and controlling the observation instrument 38. Accordingly, the instrument control unit 48 is coupled to the observation instrument 38 via at least one signal line. In addition, the embodiment in FIG. 13 is provided with a light source 320, which is coupled to the observation instrument 38 for illuminating purposes.

FIG. 13 also illustrates lines for signal and/or information exchange between observation section 306, instrument control section 308 and handling section 310

Furthermore, at least one input device 50, 244, 252 is coupled to the instrument control unit 48 via a suitable interface. It is possible to provide a plurality of input devices 50, 244, 252, so that different operators can control the handling device 10. The instrument control unit 48 and the at least one input device 50, 244, 252 are configured in such a way that they can also be used for control in a hand-guided mode of the observation instrument 38. In other words, the instrument control unit 48 coordinates the imaging and, if necessary, the image reproduction. The at least one input device 50, 244, 252 can also be used for controlling imaging parameters and image reproduction parameters.

However, according to the embodiment illustrated in FIG. 13, it is provided that the at least one input device 50, 244, 252 coupled with the instrument control unit 48 is also to be used for controlling the robotic handling unit 34. For this purpose, the instrument control unit 48 is connected to the handling control unit 46, for example via an interface 322 for information exchange. The interface 322 can also be referred to as a network interface or data bus interface.

This configuration has the effect that in a mode, in which the input device(s) 50, 244, 252 can be used to control the robotic handling unit 34 for moving the observation instrument 38 mounted thereon, the instrument control unit 48 does not itself process the corresponding control signals extensively, but instead forwards and/or passes them on to the handling control unit 46 via the interface 322. Such a mode is enabled, for example, via the input device that is arranged as enabling switch 54, using the safety device 262.

A potential advantage of this design is that the instrument control unit 48 can still be used independently and autonomously for controlling the observation instrument 38, for example in a hand-held/hand-guided mode. This also applies to any input devices 50, which are directly coupled with the instrument control unit 48. This is also possible without the handling unit 34 and its handling control unit 46.

Nevertheless, the extended scope of use can be controlled by providing the robotic handling unit 34 using one and the same input device 50. It is therefore not strictly necessary to provide an additional input device 50 for controlling the handling unit 34. Instead, the input device 50 can be used in different modes for instrument control and handling control.

This is for instance conceivable if the input device 50 is a multi-axis input device. Such input devices (cf. a so-called 3D mouse) are well suited for both control modes. The potential advantage is that one and the same arrangement can be used for a hand-held operation of the observation instrument 38 and an operation assisted by the robotic handling unit 34. It is not strictly necessary to invest twice in the observation instrument 38 and its associated instrument control unit 48. Nevertheless, simple and safe operation of the extended arrangement of the handling device 10 with the robotic handling unit 34 is ensured.

A further aspect of the present disclosure relates to the use of present operating parameters and/or general parameters of the observation instrument 38 by the control device 44, for instance by its handling control unit 46, for controlling the robotic handling unit 34. For instance, exemplary embodiments are conceivable, in which the travel speed of the robotic handling unit 34 is made dependent on operating parameters of the observation instrument 38. This can, relate to a present object distance for example. If the object distance is large, a high travel speed can be selected for moving the observation instrument 38, and if the object distance is small, a low travel speed can be selected.

Figure 14:
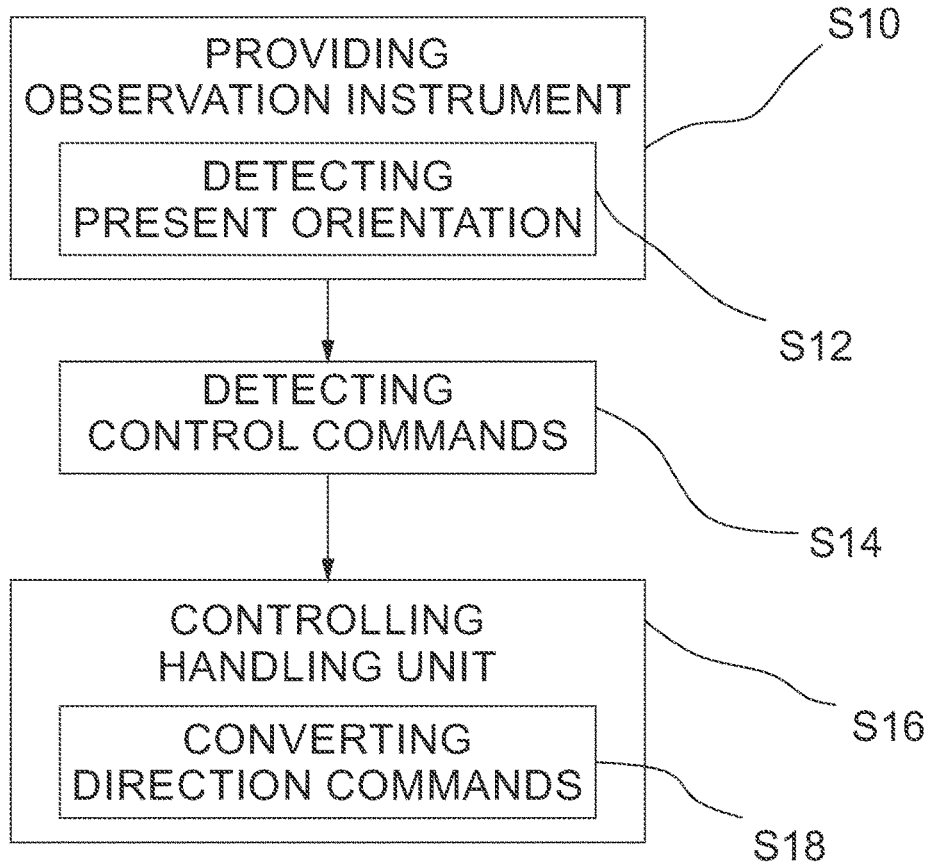
FIG. 14 is a schematic simplified block diagram illustrating an embodiment of a method for controlling a handling device.

With reference to FIG. 14, with the aid of a schematic block diagram, an exemplary embodiment of a method for controlling a handling device is elucidated. The handling device can be a medical handling device. However, it can also be a non-medical handling device.

The method comprises a step S10, which comprises the provision of an observation instrument and mounting it on an instrument holder at a robotic handling unit. The step S10 further comprises a sub-step S12, which comprises the detection of a present relative orientation, for instance an orientation (rotational orientation) of an image capturing unit. Furthermore, sub-step S12 can, at least in exemplary embodiments, comprise the detection/determination of a general orientation of the observation instrument with respect to the instrument holder. This can be derived from the type of the mounted observation instrument. In this way, a parameter set can be determined, based on which basic settings of the handling device can be made.

In a step S14, control commands that have been entered via an input device are detected, wherein the control commands relate to the selection of an image section to be reproduced. In other words, the control commands can be used to move the image section to be displayed. Other control commands are conceivable. A single-handed input device is for instance suitable for acquiring the control commands. For example, the input device is arranged as a multi-axis input device. The input device can be used both for controlling the observation instrument and the robotic handling unit.

In a step S16, the robotic handling unit is controlled in reaction to captured user inputs/control commands to change the captured image section. The manipulation of the image section can include, for example, translating, rotating and/or zooming (changing the image scale). This includes, for example, a sub-step S18, which includes the conversion of direction commands at the input device into movement instructions, for instance into movement instructions for the robotic handling unit. This is performed depending on a present orientation of the image capturing unit. In this way, an alignment between a coordinate system/orientation of the displayed image section and a coordinate system/orientation of the input device can be achieved, independent of the present configuration and orientation of the robotic handling unit. The operation can be simplified. The operator can orientate himself on the displayed image and control the handling unit intuitively on that basis.

Figure 15:
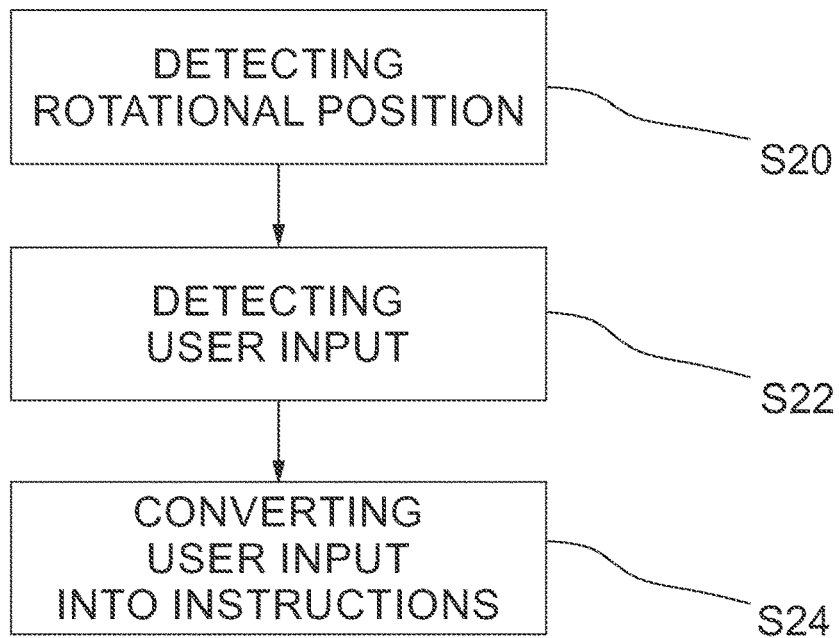
FIG. 15 is a schematically simplified block diagram to illustrate an embodiment of a method for position-corrected controlling of a handling unit under consideration of an orientation of an observation instrument.

FIG. 15 illustrates with reference to a block diagram a further exemplary embodiment of a method for controlling a handling device. The method comprises a step S20, which is concerned with the detection of a rotational position of an image capturing unit of an observation instrument. In an exemplary embodiment, the image capturing unit is a stereo image sensor. The detection of the rotational position can be performed via a rotation position sensor and/or indirectly via the control of a rotary drive.

In a further step S22, the detection of a user input at the input device takes place. This can include a manipulation of a multi-axis input element, for example. In other words, the input element may have several degrees of freedom for linear and/or pivot motions. For example, the input at the input device have to goal of moving, rotating, or pivoting the currently displayed image section. This is subject to a corresponding movement of the observation instrument held by the handling unit.

In a further step S24, a coordinate transformation is carried out for this purpose in order to convert the operator input into movement instructions for the robotic handling unit. This is for instance done while taking into account the rotational position of the image capturing unit. This results in an arrangement, which allows an operator to orientate himself by the currently displayed image section, which reflects the current orientation of the image capturing unit. The operator does not have to consider the current orientation of the handling unit and/or the observation instrument mounted thereon when making inputs at the input device for manipulating the image section. Instead, this is done automatically, in the background, by a coordinate transformation.

Based on the user input, the detected rotational position of the image capturing unit and the present orientation of the handling unit with the observation instrument, an interpolated movement path for the handling unit, based on which the handling unit is controlled, can be derived in response to the user input.

What is claimed is:

1. A medical handling device, comprising:
an instrument holder that holds an observation instrument that comprises an image capturing unit that captures an image section,
a robotic handling unit that supports the instrument holder,
a control device that comprises a handling control unit that controls the robotic handling unit and an instrument control unit that controls the observation instrument, and
an input device that is coupled to the control device that selects an image section to be displayed,
wherein the control device is adapted to control the robotic handling unit in response to user inputs at the input device to change the selected image section,
wherein the control device is adapted to convert operating commands at the input device into movement instructions, depending on a present orientation of the image capturing unit, wherein the movement instructions at least include a digital shifting of the selected image section without a movement of the observation instrument, wherein the digital shifting is enabled since the captured image section is larger in size than the selected image section,
wherein the input device is arranged as a single-handed multi-axis input device that allows operating movements in the form of travel motions or pivot motions in at least two axes, in order to detect movement signals for the two-dimensional movement of the image section in a plane, and
wherein the control device is adapted to align the two movement axes of the input device with the present orientation of the image capturing unit, so that operating movements of an input element of the input device result in movements of the displayed image section in the same direction.

2. The handling device of claim 1, further comprising:
a display unit that displays the selected image section,
wherein the control device takes into account the present orientation of the image capturing unit when controlling the display unit for reproducing the image section.

3. The handling device of claim 1,
wherein the control device detects the present orientation of the image capturing unit and, depending thereon, performs a mapping between an input device coordinate system and a coordinate system of the robotic handling unit, which reflects the orientation of the image capturing unit.

4. The handling device of claim 1,
wherein the observation instrument comprises an orientation sensor that detects the orientation of the image capturing unit.

5. The handling device of claim 1,
wherein the observation instrument comprises a stereo image capturing unit having two image sensors.

6. The handling device of claim 1,
wherein the image capturing unit is rotatable in the observation instrument.

7. The handling device of claim 1,
wherein the control device is adapted to digitally rotate the image section captured by the image capturing unit.

8. The handling device of claim 1,
wherein the control device is adapted to perform a mapping between the orientation of the image capturing unit and movement axes for the input at the input device in such a way that directions of movement of the image section that is displayed by the display unit are brought into alignment with direction instructions at the input device.

9. The handling device of claim 1,
wherein the control device is adapted to convert the movement instructions into control commands for movement axes of the robotic handling unit.

10. The handling device of claim 1,
wherein the robotic handling unit comprises multi-link kinematics having a plurality of coupling links, which are controlled by the handling control unit of the control device.

11. The handling device of claim 1,
wherein the input device detects operating movements at least in the form of a rotation about a longitudinal axis or a translation along the longitudinal axis in order to detect movement signals for controlling a zoom function and for focus adjustment.

12. The handling device of claim 1,
wherein the handling control unit of the control device is adapted to move the displayed image section in a first operating mode in response to operating commands at the input device via movements of the robotic handling unit, and
wherein the instrument control unit of the control device is adapted to move the displayed image section in a second operating mode in response to operating commands at the input device via the digital shifting of the displayed image section in a captured recording area.

13. The handling device of claim 1,
wherein the input device is operable in a first operating mode that controls the observation instrument and in a second operating mode that controls the robotic handling unit, and
wherein the handling device further comprises an enabling switch that activates the second operating mode, in which the robotic handling unit is movable in response to input commands at the input device.

14. The handling device of claim 1,
wherein the control device is adapted to perform an initialization procedure in order to acquire configuration information relating to the supported observation instrument,
wherein the initialization comprises a query via the instrument control unit, and
wherein the configuration information is transmitted to the handling control unit and taken into account for the control of the robotic handling unit.

15. The handling device of claim 1,
wherein the control device is adapted to mirror the displayed image section, and
wherein the implementation of operating commands at the input device takes the mirroring into account.

16. The handling device of claim 1,
wherein the control device is adapted to control the robotic handling unit in such a way that the observation instrument is pivotable about a virtual pivot axis, which is arranged parallel to the image capturing unit, by interpolated movement of the robotic handling unit.

17. The handling device of claim 1,
wherein the control device is adapted to operate the robotic handling unit in a direct control mode in order to move and align the observation instrument in space,
wherein operating commands are generated at the robotic handling unit by, acting on an element of the robotic handling unit, which is adjacent to the instrument, and
wherein the handling control unit is adapted to control the robotic handling unit in such a way that the observation instrument follows the induced movement.

18. The handling device of claim 17,
wherein the operating commands in the direct control mode are provided via an operating element, which generates an enabling signal for the direct control mode via a sensor.

19. A medical handling device, comprising:
an instrument holder that holds an observation instrument that comprises an image capturing unit that captures an image section,
a robotic handling unit that supports the instrument holder,
a control device that comprises a handling control unit that controls the robotic handling unit and an instrument control unit that controls the observation instrument, and
an input device that is coupled to the control device that selects an image section to be displayed,
wherein the control device is adapted to control the robotic handling unit in response to user inputs at the input device to change the selected image section,
wherein the control device is adapted to convert operating commands at the input device into movement instructions for the robotic handling unit, depending on a present orientation of the image capturing unit, wherein the movement instructions at least include a digital shifting of the selected image section without a movement of the observation instrument, wherein the digital shifting is enabled since the captured image section is larger in size than the selected image section,
wherein the input device is arranged as a multi-axis input device that allows operating movements in the form of travel motions or pivot motions in at least two axes, in order to detect movement signals for the two-dimensional movement of the image section in a plane, and
wherein the control device is adapted to align the two movement axes of the input device with the present orientation of the image capturing unit, so that operating movements of an input element of the input device result in movements of the displayed image section in the same direction.

20. A method that controls a handling device comprising a robotic handling unit having an instrument holder and an observation instrument mounted thereon, and comprising an image capturing unit that captures an image section, the method comprising:
providing an observation instrument at the instrument holder,
acquiring control commands that select an image section to be displayed via an input device that is coupled to a control device that controls the observation instrument and that controls the robotic handling unit, wherein the input device is arranged as a single-handed multi-axis input device that allows operating movements in the form of travel motions or pivot motions in at least two axes, in order to detect movement signals for the two-dimensional movement of the image section in a plane, and
controlling the robotic handling unit in response to user inputs at the input device to change the selected image section, wherein the movement instructions at least include a digital shifting of the selected image section without a movement of the observation instrument, wherein the digital shifting is enabled since the captured image section is larger in size than the selected image section, comprising:

converting direction commands at the input device into movement instructions, depending on the present orientation of the image capturing unit, aligning the two movement axes of the input device with the present orientation of the image capturing unit, so that operating movements of an input element of the input device result in movements of the displayed image section in the same direction.

* * * * *